United States Patent
Martin et al.

(10) Patent No.: US 8,586,973 B2
(45) Date of Patent: Nov. 19, 2013

(54) HOST MATERIAL FOR LIGHT-EMITTING DIODES

(75) Inventors: Roland Martin, St-Stevens-Woluwe (BE); Veronique Mathieu, Wavre (BE); Victor Sorokin, Cincinnati, OH (US); Praveen Bachawala, Cincinnati, OH (US); Wieslaw Adam Mazur, Mason, OH (US); Jonathan Maunoury, Brussels (BE)

(73) Assignee: Solvay SA, Brussels (BE)

( * ) Notice: Subject to any disclaimer, the term of this patent is extended or adjusted under 35 U.S.C. 154(b) by 277 days.

(21) Appl. No.: 13/124,209

(22) PCT Filed: Oct. 15, 2009

(86) PCT No.: PCT/EP2009/063519
§ 371 (c)(1),
(2), (4) Date: Apr. 14, 2011

(87) PCT Pub. No.: WO2010/043693
PCT Pub. Date: Apr. 22, 2010

(65) Prior Publication Data
US 2011/0198579 A1   Aug. 18, 2011

Related U.S. Application Data

(60) Provisional application No. 61/105,838, filed on Oct. 16, 2008.

(30) Foreign Application Priority Data

Nov. 27, 2008 (EP) .................................... 08170151

(51) Int. Cl.
*H01L 51/30* (2006.01)

(52) U.S. Cl.
USPC .................................... 257/40; 257/E51.024

(58) Field of Classification Search
USPC ............................................. 257/40, E51.024
See application file for complete search history.

(56) References Cited

U.S. PATENT DOCUMENTS

| 2003/0205696 A1 | 11/2003 | Thoms et al. |
| 2007/0173657 A1 | 7/2007 | Chen et al. |

(Continued)

FOREIGN PATENT DOCUMENTS

| JP | 2004311411 A | 11/2004 |
| JP | 2008-109103 | 5/2008 |

(Continued)

OTHER PUBLICATIONS

Lia. et. al.—"Novel fluorene/carbazole hybrids with steric bulk as host materials for blue organic electrophosphorescent devices", 2007, Tetrahedron 63, Elsevier, pp. 10161-10168; 8 pgs.

(Continued)

*Primary Examiner* — Marc Armand
(74) *Attorney, Agent, or Firm* — Foley & Lardner, LLP

(57) ABSTRACT

The present invention relates to a host material comprising a compound having two carbazole moieties which is suitable for blue-emitting OLEDs. Surprisingly, it has been found that when appropriate substituents are present in the carbazole structure, the solubility of the compounds can be improved without any adverse effect on the OLED performance. The present invention further relates to the use of the host materials and to an organic light emitting device comprising the host material.

20 Claims, 5 Drawing Sheets

(56) References Cited

U.S. PATENT DOCUMENTS

2007/0262703 A1* 11/2007 Tsai et al. .................. 313/503
2007/0262704 A1* 11/2007 Tsai et al. .................. 313/503

FOREIGN PATENT DOCUMENTS

| JP | 2008109103 A | 5/2008 |
|----|--------------|--------|
| WO | WO 2009/080799 A2 | 2/2009 |
| WO | WO 2010/043691 A1 | 4/2010 |

OTHER PUBLICATIONS

Wu. et. al.—"The Quest for High-Performance Host Materials for Electrophosphorescent Blue Dopants", 2007, Adv. Funct. Mater., 17, 1887-1895; 9 pgs.

Thoms. et. al.—"Improved host material design for phosphorescent guest—host systems", 2003, Thin Solid Films 436, Elsevier, 264-268; 5 pgs.

Maruyama et al.—"Synthesis of Novel Carbazolylacetylene-Derived Macrocycles". Synthesis, 2001, No. 12: 1794-1799; 6 pgs.

U.S. Appl. No. 13/124,251, Roland Martin et al.

* cited by examiner

HOST MATERIAL FOR LIGHT-EMITTING DIODES

CROSS REFERENCE TO RELATED APPLICATIONS

This application is a U.S. national stage entry under 35 U.S.C. §371 of International Application No. PCT/EP2009/063519 filed Oct. 15, 2009, which claims priority to U.S. provisional application 61/105,838 filed on Oct. 16, 2008 and to European patent application 08170151.8 filed on Nov. 27, 2008, both of these applications being incorporated herein by reference in their entirety for all purposes.

TECHNICAL FIELD

The present invention relates to a host material for light-emitting diodes, to the use of such host material, and to a light-emitting device capable of converting electrical energy into light.

BACKGROUND

Recently, various display and lighting devices have been under active study and development, particularly those based on electroluminescence (EL) from organic materials.

Many organic materials exhibit fluorescence (i.e., luminescence from a symmetry-allowed process) from singlet excitons. Since this process occurs between states of equal symmetry, it may be very efficient. On the contrary, if the symmetry of an exciton is different from that of the ground state, then the radioactive relaxation of the exciton is disallowed and luminescence will be slow and inefficient. Because the ground state is usually anti-symmetric, the decay from a triplet breaks the symmetry. The process is thus disallowed and the efficiency of EL is very low. Therefore, the energy contained in the triplet state is mostly wasted.

The luminescence from a symmetry-disallowed process is known as phosphorescence. Characteristically, phosphorescence may persist up to several seconds after excitation due to the low probability of the transition, in contrast to fluorescence which shows rapid decay. The use of phosphorescent materials has been a major breakthrough in boosting electroluminescence efficiency because they allow for the simultaneous harvesting of both singlet and triplet excitons. Selecting a suitable host material for the phosphorophore dopants remains one of the critical issues in phosphorescence-based OLEDs. The host material is important because efficient exothermic energy transfer from the host material to the dopant phosphorophore depends on whether the triplet-state energy of the host is greater than that of the dopant.

Well known host materials for guest-host systems include hole-transporting 4,4'-N,N'-dicarbazol-biphenyl (CBP) and electron-transporting aluminum 8-hydroxyquinoline (AlQ$_3$), which have both been used in OLEDs. However, the known host materials are not suitable for all phosphorescent guests. For example, the host compound for phosphorescent emitters must fulfil an important condition that the triplet energy of the host shall be higher than that of the phosphorescent emitter. In order to provide efficient phosphorescence from the phosphorescent emitter, the lowest excited triplet state of the host has to be higher in energy than the lowest emitting state of the phosphorescent emitter. Since emission from the phosphorescent emitter is desired, the lowest excited state has to be from the phosphorescent emitter, not the host compound. As such, there continues to be a need in the art for suitable host materials for guests which have short emission wavelengths in the light spectrum, e.g., in the blue region of the spectrum.

Several host materials for better phosphorescent emission have been reported. Due to their charge conducting ability, photophysical and redox properties, sufficiently large triplet energies and carrier-transport properties, carbazole-based compounds have been actively studied.

For example, U.S. Patent Application Publication No. US 2003/205696 assigned to Canon KK discloses guest-host emissive systems suitable for use with organic light emitting devices in which the host material comprises a compound having a carbazole core with an electron-donating species bonded to nitrogen, aromatic amine groups or carbazole groups bonded to one or more of the carbon atoms, a large band gap potential, and high-energy triplet excited states. Such materials permit short-wavelength phosphorescent emission by an associated guest material, and the combination of said materials with emissive phosphorescent organometallic compounds such as platinum complexes is useful in the fabrication of organic light emitting devices.

Li et al., "Novel fluorene/carbazole hybrids with steric bulk as host materials for blue organic electrophosphorescent devices," *Tetrahedron*, 63(41):10161-10168 (2007) discloses the use of sterically hindered spacers in phosphorescent dopants to prevent or reduce the problem of self-quenching in organic electrophosphorescence devices. Novel fluorene/carbazole hybrids with tert-butyl substitutions, namely 9,9-bis [4-(3,6-di-tert-butylcarbazol-9-yl)phenyl]fluorene (TBCPF) and 9,9-bis[4-(carbazol-9-yl)phenyl]-2,7-di-tert-butylfluorene (CPTBF), reportedly exhibit not only high triplet energy (>2.8 eV) but also high glass transition temperature (Tg) (>160° C.) and thermal stability.

Further, Wu et al., "The Quest for High-Performance Host Materials for Electrophosphorescent Blue Dopants," *Adv. Funct. Mater.*, 17: 1887-1895 (2007) discloses 3,5-di(N-carbazolyl)tetraphenylsilane (SimCP) and N,N'-dicarbazolyl-3, 5-benzene (mCP) as host materials for phosphorescent blue dopants, while Thoms et al., "Improved host material design for phosphorescent guest-host systems," *Thin Solid Films* 436: 264-268 (2003) discloses a series of carbazole-based compounds as host materials in an iridium phosphor-based guest-host organic light emitting diode and the results of semi-empirical calculations.

However, none of the above-disclosed materials meet all the requirements necessary for OLED application, e.g., suitable energy level, charge transport ability, processability from a solution with uniform film formation, ability to form an amorphous phase, ability for good dopant dispersion, morphological stability (high Tg), thermal and electrochemical stabilities under operational conditions of the device. Therefore, there has been a need to develop new host materials which are capable of satisfying all of the requirements indicated above.

DISCLOSURE OF THE INVENTION

Figure 1:
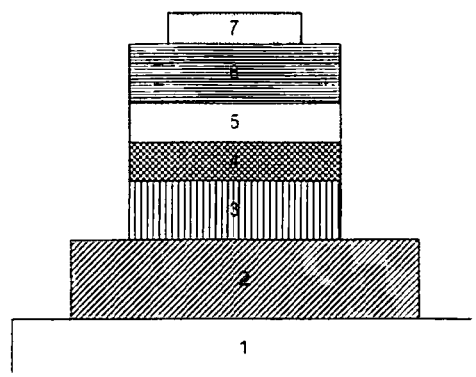
FIG. 1 shows a cross-sectional view of a display device containing the organic light emitting device of the present invention.

One aspect of the present invention relates to a host material comprising a carbazole-based compound as described below.

Another aspect of the present invention relates to the use of the host material for the emissive layer and to an organic light emitting device comprising the host material.

The present invention provides a host material which comprises the compound of Formula I:

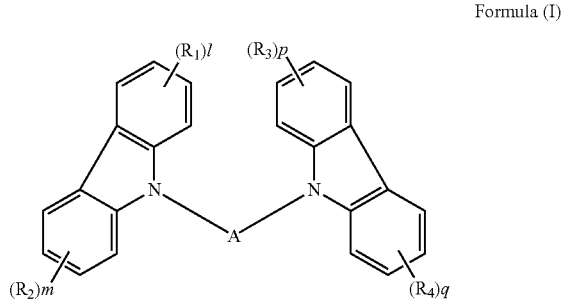

Formula (I)

where:
A is an organic divalent radical;
$R_1$, $R_2$, $R_3$, and $R_4$ are non-conjugate substituents, the same or different at each occurrence and selected from the group consisting of:
  trityl
  halogen;
  nitro;
  cyano;
  —$COOR_5$;
  alkoxy or dialkylamino group having from 1 to 20 carbon atoms where one or more nonadjacent —$CH_2$— groups may be replaced by —O—, —S—, —$NR_6$—, —$CONR_7$—, or —COO—, and where at least one hydrogen atom may be replaced by halogen; and
  —$SiR_8R_9R_{10}$;
where $R_5$, $R_6$, $R_7$, $R_8$, $R_9$, and $R_{10}$ are the same or different at each occurrence and independently selected from the group consisting of —H, halogen, nitro, cyano, straight or branched $C_{1-20}$-alkyl, $C_{3-20}$-cyclic alkyl, straight or branched $C_{1-20}$-alkoxy, $C_{1-20}$ 20-dialkylamino, $C_{4-14}$-aryl, $C_{4-14}$-aryloxy, and $C_{4-14}$-heteroaryl, which may be substituted by one or more non aromatic radicals, where a plurality of $R_1$, $R_2$, $R_3$, $R_4$, $R_8$, $R_9$, and $R_{10}$ may in turn together form a mono- or polycyclic ring, optionally aromatic; and
l, m, p, and q are the same or different at each occurrence and represent an integer from 0 to 4 where l+m+p+q>0.

In some embodiments of the present invention, A is a divalent radical comprising at least one structural unit selected from the group consisting of five- or six-membered aryl or heteroaryl rings and fused rings. Specifically, A is a divalent radical selected from the group consisting of naphthyl, anthryl, phenanthryl, benzimidazolyl, carbazolyl, fluorenyl, pyridazinyl, quinolinyl, isoquinolinyl, quinoxalinyl, benzothiophenyl, phthalazinyl, quinazolinyl, benzimidazolyl, benzoxazolyl, and phenanthridinyl.

Surprisingly, it has been found that, when an appropriate substituent such as a trialkylsilyl group is introduced to the carbazole structure of the compound of the present invention, its solubility and processability can be improved without any adverse effects on the other properties, such as color, efficiency, etc.

In another embodiment of the present invention, A is a divalent radical of Formula II:

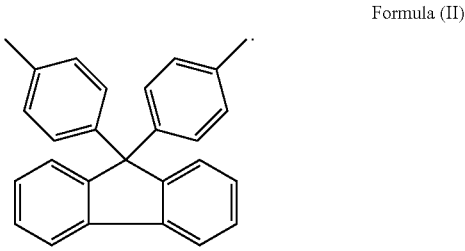

Formula (II)

In another embodiment of the present invention, A is a divalent radical of Formula III:

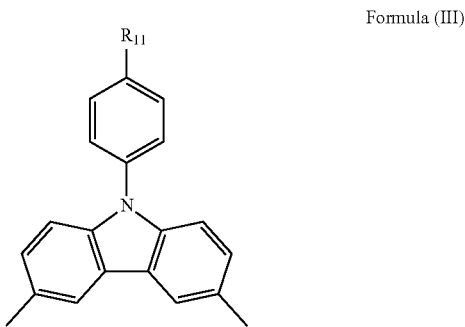

Formula (III)

where $R_{11}$ is an tert-alkyl, fluorinated alkyl, trityl, alkoxy, or halogen group.

In some embodiments of the present invention, each of $R_1$, $R_2$, $R_3$, and $R_4$ is —$SiR_8R_9R_{10}$, where $R_8$, $R_9$, and $R_{10}$ are the same or different at each occurrence and independently selected from the group consisting of alkyl groups and aryl groups.

In another embodiment of the present invention, each of $R_8$, $R_9$, and $R_{10}$ is an isopropyl group and each of l, m, p, and q is 1.

Specifically, some embodiments of the present invention include the following compounds represented by Formulae (IV) to (XI):

Formula (IV)
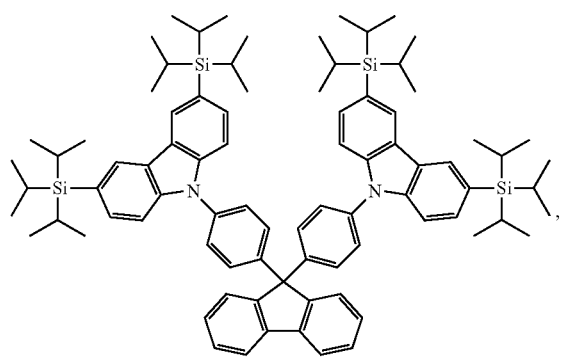
Formula (V)
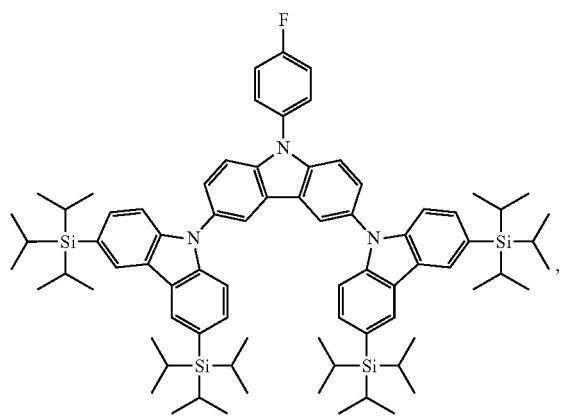
Formula (VI)
Formula (VII)
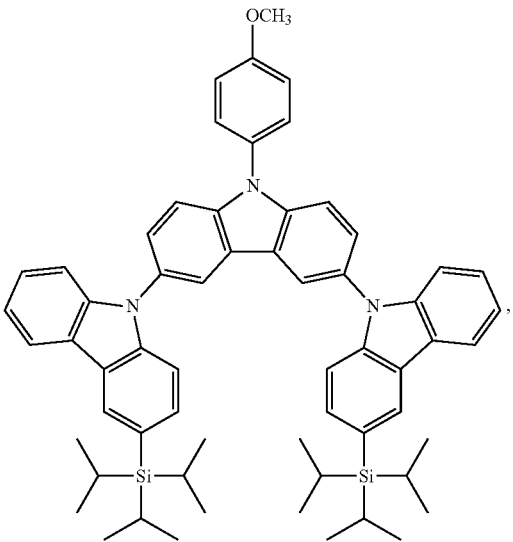
Formula (VIII)
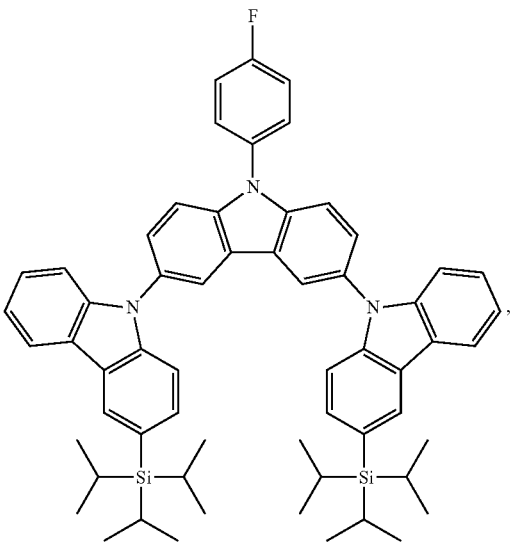
Formula (IX)
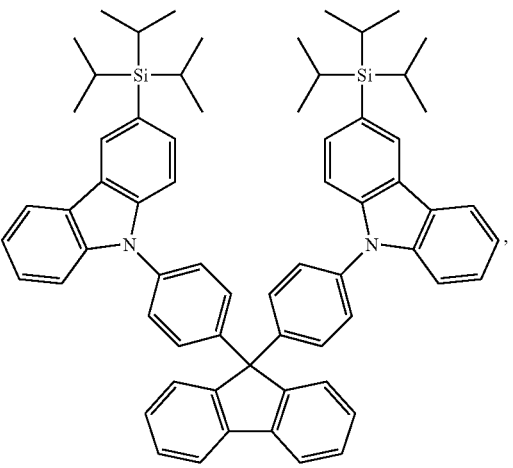

Formula (X)

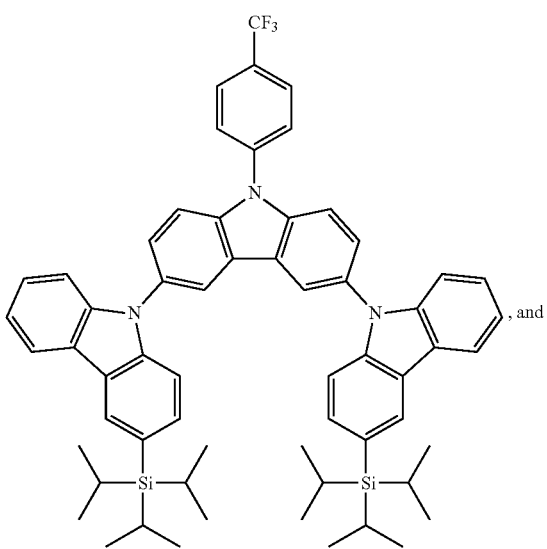, and

Formula (XI)

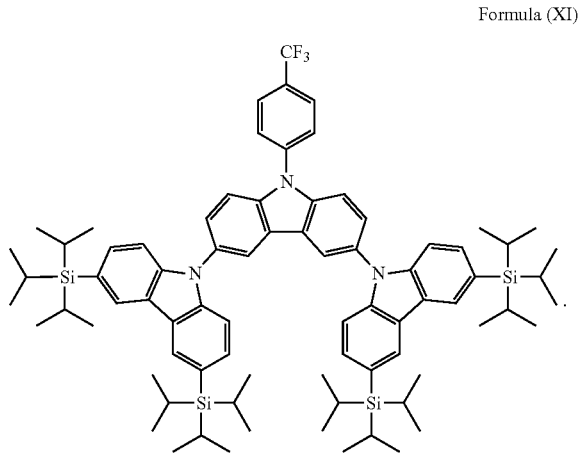 [SMILES: CC(C)[Si](c1ccc2c(c1)c1cc([Si](C(C)C)(C(C)C)C(C)C)ccc1n2-c1ccc2c(c1)c1cc(-n3c4ccc([Si](C(C)C)(C(C)C)C(C)C)cc4c4cc([Si](C(C)C)(C(C)C)C(C)C)ccc43)ccc1n2-c1ccc(C(F)(F)F)cc1)(C(C)C)C(C)C]

Generally, according to the embodiments of the present invention, the compound of Formula I can be prepared by the following reaction scheme, i.e., via a Ullman C—N coupling reaction of a dehalogenated organic compound with the corresponding carbazole derivative.

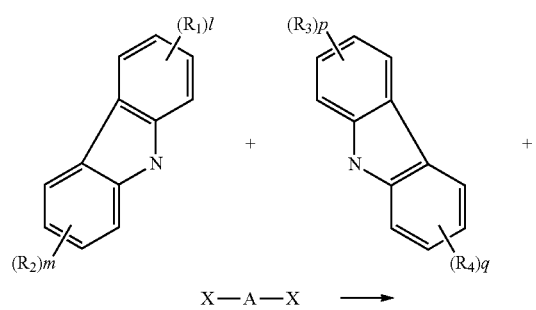

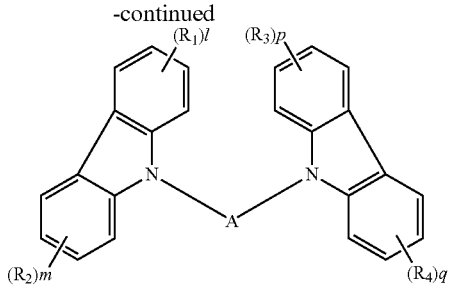

Formula (I)

In some embodiments, copper/18-crown-6 is used as a catalyst and potassium carbonate as a base.

In order to introduce substituents $R_1$ to $R_4$ to carbazole rings, any method known in the art can be used. In some embodiments of the present invention, a free imide nitrogen of dibrominated carbazole is initially protected by benzyl halide and further reacted with trialkylsilyltriflate in the presence of n-butyllithium, followed by deprotection, to give trialkylsilyl-substituted carbazole derivatives.

The present invention is also directed to the use of the above compounds as host material in an emissive layer, where they function with an emissive material in an emissive layer in an organic light emitting device.

Suitable guest emissive (dopant) materials can be selected from those known in the art and hereafter developed including, without limitation, bis(2-phenylpyridine)iridium complexes, which exhibit a phosphorescent emission in the blue region of the spectrum. In specific embodiments, the guest exhibits a phosphorescent emission in the pure blue region of the spectrum.

If the emissive material is used as a dopant in a host layer comprising the compound of the present invention, it is generally used in an amount of at least 1% wt, specifically at least 3% wt, and more specifically at least 5% wt, with respect to the total weight of the host and the dopant. Further, it is generally used in an amount of at most 25% wt, specifically at most 20% wt, and more specifically at most 15% wt.

The present invention is also directed to an organic light emitting device (OLED) comprising an emissive layer, where the emissive layer comprises the host material described above. The OLED can also comprise an emissive material (where the light emitting material is present as a dopant), where the emissive material is adapted to luminesce when voltage is applied across the device.

The OLED generally comprises:
a glass substrate;
a generally transparent anode, such as an indium-tin oxide (ITO) anode;
a hole transporting layer (HTL);
an emissive layer (EML);
an electron transporting layer (ETL); and
a generally metallic cathode such as an Al layer.

For the hole conducting emissive layer, an exciton blocking layer, notably a hole blocking layer (HBL), may be present between the emissive layer and the electron transporting layer. For the electron conducting emissive layer, an exciton blocking layer, notably an electron blocking layer (EBL), may be present between the emissive layer and the hole transporting layer.

The emissive layer is formed with a host material comprising the compound of the present invention where the light emitting material exists as a guest. The emissive layer may further comprise an electron-transporting material selected from the group consisting of metal quinoxolates (e.g., aluminium quinolate (Alq$_3$), lithium quinolate (Liq)), oxadiazoles, and triazoles. A suitable example of the host material, without limitation, is 4,4'-N,N'-dicarbazole-biphenyl ["CBP"], which can be represented by the following formula:

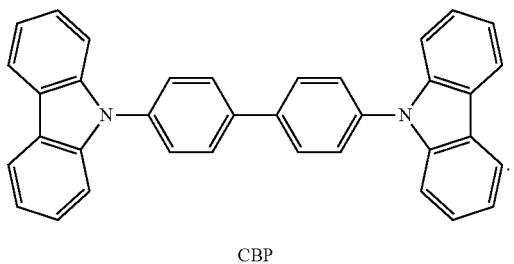 [SMILES: c1ccc2c(c1)c1ccccc1n2-c1ccc(-c2ccc(-n3c4ccccc4c4ccccc43)cc2)cc1 ; "CBP"]

CBP

Optionally, the emissive layer may also contain a polarization molecule that is present as a dopant in the host material and has a dipole moment which generally affects the wavelength of the light emitted when the light emitting material used as a dopant luminesces.

The layer formed from the electron transporting material is used to transport electrons into the emissive layer comprising the light emitting material and the optional host material. The electron transporting material may be an electron-transporting matrix selected from the group consisting of metal quinoxolates (e.g., Alq$_3$ and Liq), oxadiazoles, and triazoles. A suitable example of the electron transporting material is, without limitation, tris-(8-hydroxyquinoline)aluminum of formula ["Alq$_3$"]:

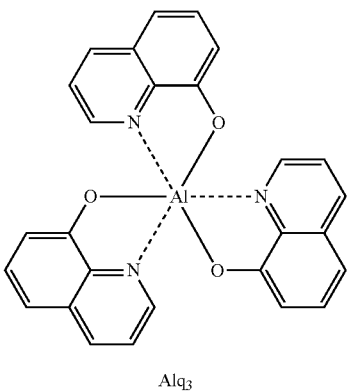

Alq$_3$

The layer formed from the hole transporting material is used to transport holes into the emissive layer comprising the light emitting material and the optional host material. A suitable example of the hole transporting material, without limitation, is 4,4'-bis[N-(1-naphthyl)-N-phenylamino]biphenyl ["α-NPD"] of the following formula:

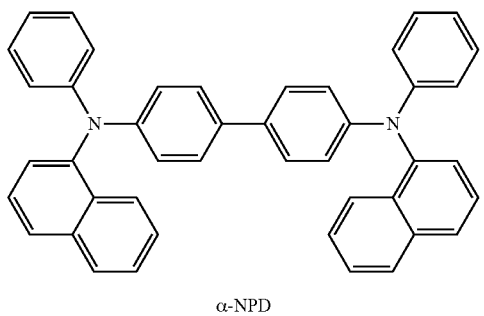 [SMILES: c1ccc(N(c2ccc(-c3ccc(N(c4ccccc4)c4cccc5ccccc45)cc3)cc2)c2cccc3ccccc23)cc1]

α-NPD

The use of the exciton blocking layer ("barrier layer") to confine excitons within the luminescent layer ("luminescent zone") is advantageous. For a hole-transporting host, the blocking layer may be placed between the emissive layer and the electron transport layer. A suitable example of the material for the barrier layer, without limitation, is 2,9-dimethyl-4,7-diphenyl-1,10-phenanthroline (also referred to as bathocuproine or "BCP"), which has the following formula:

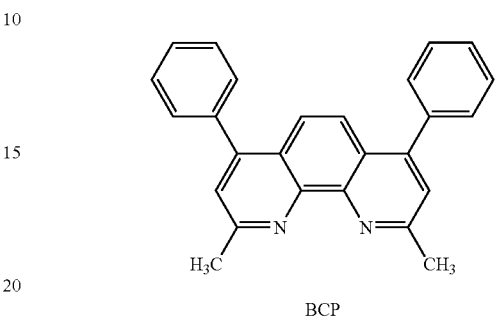

BCP

As depicted in FIG. 1, in some embodiments, the OLED according to the present invention has a multilayer structure where: 1 is a glass substrate; 2 is an ITO layer; 3 is an HTL layer comprising α-NPD; 4 is an EML comprising host material and the light emitting material as dopant in an amount of about 8% wt with respect to the total weight of the host plus dopant; 5 is an HBL comprising BCP; 6 is an ETL comprising Alga; and 7 is an Al layer cathode.

EXAMPLES

Hereinafter, the present invention will be explained in detail with reference to examples and comparative examples. These examples, however, should not in any sense be interpreted as limiting the scope of the present invention. Further, units are expressed by weight unless otherwise described.

All raw materials were purchased from Aldrich (U.S.A.), AlfaAesar (U.S.A.) or TCI (Japan). Drum solvents (e.g., EtOAc, hexane, THF, acetonitrile, DMF, dichloromethane) were used herein and were purchased from Mallinckrodt (U.S.A.) and Tedia. Freshly distilled tetrahydrofurane (over LiAlH$_4$) was used as the solvent for metalation reactions. All reagents were weighed and mixed in a glove box under nitrogen.

All $^1$H, $^{13}$C, and $^{19}$F NMR spectra were recorded on a Bruker Avance III 400 NMR spectrometer at 400 MHz, 100 MHz, and 376 MHz, respectively, for solutions in CDCl$_3$ or DMSO-d$_6$. All in-process HPLC analyses were performed using a Hitachi Elite LaChrome machine. The reference wavelengths used were 245 nm and 220 nm. The LC/MS data were recorded on a Varian 1200L LC/MS, while the GC/MS data were recorded on an Agilent 6890 GC system. A CombiFlash Companion was used for the isolation and purification of the intermediates and final compounds. Thin layer chromatography was carried out using 2.5×7.5 cm Merck 60 F-254 plates, and the elution solvents were hexane, EtOAc/hexane, and hexane/dichloromethane mixtures. The TLC plates were visualized by UV, iodine, and a 20% ethanol solution of phosphomolybdic acid, followed by heating on a hot plate. All experiments were carried out under a nitrogen or argon atmosphere.

Example 1

Synthesis of 9'-(4-Methoxy-phenyl)-3,6,3'',6''-tetrakis-triisopropylsilanyl-9'-[9,3';6',9'']tercarbazole (Compound VI)

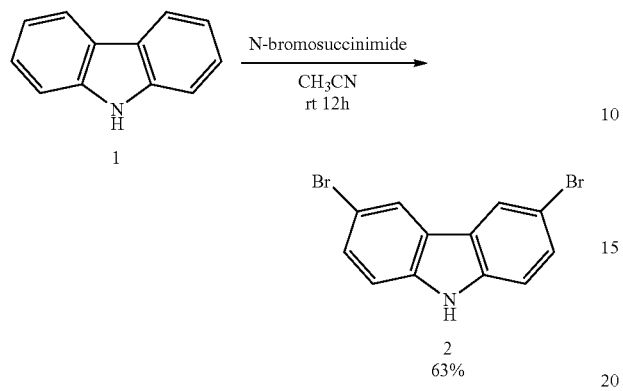

A 2 L dry round bottom flask was charged with carbazole 1 (90.7 g, 0.543 mol) and 1 L dry acetonitrile and stirred for one hour at room temperature under nitrogen, where most of the carbazole dissolved. N-bromosuccinimide (193.1 g, 1.084 mol) was added to the suspension neat in portions, where the reaction was exothermic. The mixture was immediately cooled in an ice-water bath following the addition. The mixture was left to be stirred overnight at room temperature. The resulting white precipitate was filtered, washed with acetonitrile, and dried to yield 112.0 g (63%) 3,6-dibromocarbazole 2.

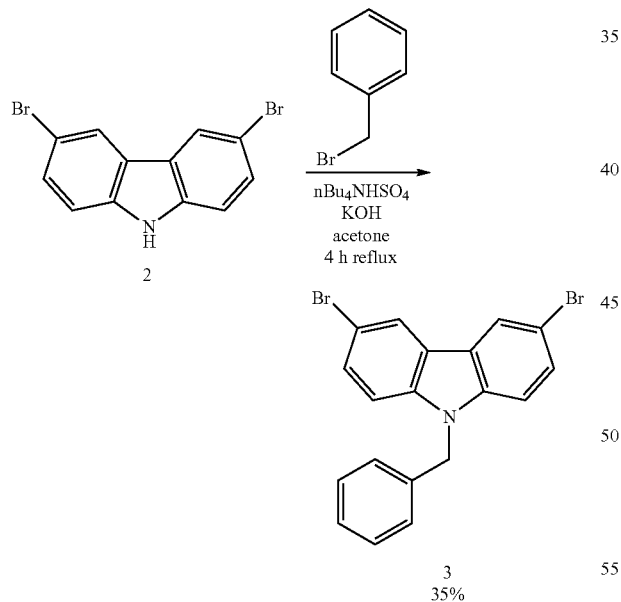

3,6-Dibromocarbazole 2 (112.0 g, 0.344 mol), benzyl bromide (41 ml, 0.344 mol), and nBu$_4$NHSO$_4$ were mixed in 200 ml of acetone and stirred at room temperature under nitrogen until dissolved. KOH (19.3 g, 0.344 mol) was then added to the above transparent solution and the resultant mixture was refluxed for 4 hours, where a white precipitate was observed. The hot mixture was concentrated to remove the majority of acetone. Upon cooling, additional white precipitate appeared. The precipitate was filtered, dissolved in methyl-t-butyl ether, washed with water, dried over Na$_2$SO$_4$, and concentrated to yield a major amount of pure N-benzyl-3,6-dibromocarbazole 3. The filtrate was also washed with water and extracted with methyl-t-butyl ether, dried over Na$_2$SO$_4$, concentrated, and purified over 120 g SiO$_2$ with hexane and hexane:ethylacetate (95:5) eluents to yield a minor amount of pure N-benzyl-3,6-dibromocarbazole 3. The combined yield from crystallization and chromatography was 49 g (35%) of N-benzyl-3,6-dibromocarbazole 3.

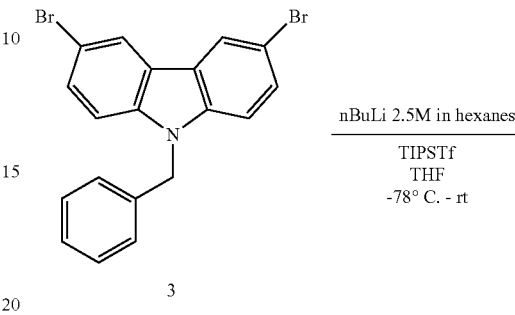

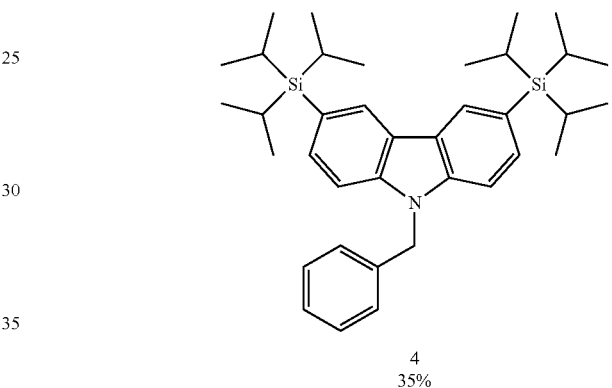

A 2 L dry round bottom flask was charged with N-benzyl-3,6-dibromocarbazole 3 (49 g, 0.118 mol) and 1 L of dry THF was added. The mixture was stirred until N-benzyl-3,6-dibromocarbazole 3 was dissolved. The mixture was then cooled to −78° C. and 2.5 M n-BuLi in hexanes (104 ml, 0.26 mol) was added dropwise. The mixture was stirred at −78° C. for 15 min and triisopropylsilyl-trifluoromethyl sulfonate (66 ml, 0.26 mol) was added. The mixture was left to warm up to room temperature overnight. The mixture was then quenched with sat. NH$_4$Cl, extracted with methyl-t-butyl ether, dried over Na$_2$SO$_4$, filtered, concentrated, and purified over a 330 g SiO$_2$ column to yield 9-benzyl-3,6-bis-triisopropylsilanyl-9H-carbazole 4 23.0 g (35%) as a transparent oil.

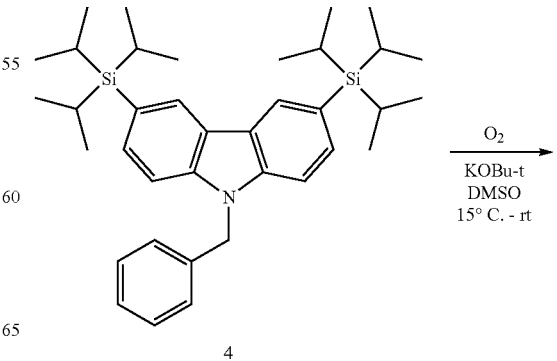

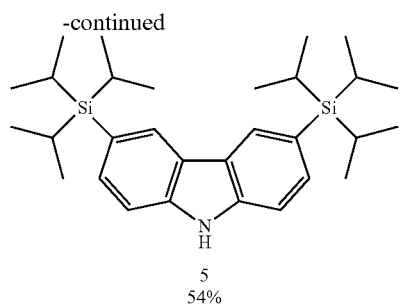

5
54%

A 500 ml dry round bottom flask was charged with 9-benzyl-3,6-bis-triisopropylsilanyl-9H-carbazole 4 (23.0 g, 0.04 mol) and the oil was suspended in 100 ml DMSO. The suspension was cooled in an ice water bath (~15° C.) and 1M KOBu-t in THF (240 ml, 0.24 mol) was added via a syringe under nitrogen. Oxygen started to bubble in the mixture and the nitrogen line was suppressed. While the oxygen bubbling was taking place, the mixture was left to warm up to ~20° C. and cooling continued with only water. The oxygen bubbling continued until the starting material (TLC) disappeared, i.e., after ~30 min. Water was added to the mixture and the mixture was extracted with 5×200 ml ethylacetate. To remove the benzoic acid organic layer, the mixture was washed with sat. NaHCO₃, followed by brine washing. The organic layer was then dried over Na₂SO₄, filtered, concentrated, and purified over a 330 g SiO₂ column with hexane and hexane:ethylacetate (95:5) eluents. Appropriate fractions were collected to yield a white solid of 3,6-bis-triisopropylsilanyl-carbazole 5 10.0 g (54%).

A mixture of 3,6-bis-triisopropylsilanyl-carbazole 5 (5.0 g, 0.011 mol), 3,6-diiodo-9-(4-methoxy-phenyl)-9H-carbazole 6 (2.6 g, 0.005 mol), K₂CO₃ (2.9 g, 0.021 mol), Cu nano powder (0.6 g, 0.011 mol), and 18-crown-6 (2.7 g, 0.011 mol) in 50 ml 1,2-dichlorobenzene was degassed with argon while stirring. The reaction mixture was then refluxed under argon for 12 hours at 178° C. The crude mixture was filtered and the residue was washed with CH₂Cl₂. The combined filtrates were concentrated and the residue was purified by chromatography on a 120 g SiO₂ column once and five times on a 160 g Al₂O₃ column with a cyclohexane eluent at a flow rate of 20 ml/min. Appropriate pure fractions were collected to yield 1.8 g of (30%) white powder of 9'-(4-methoxy-phenyl)-3,6,3",6"-tetrakis-triisopropylsilanyl-9'H-[9,3';6',9"]tercarbazole 7.

Example 2

Synthesis of 9'-(4-Fluoro-phenyl)-3,6,3",6"-tetrakis-triisopropylsilanyl-9'H-[9,3';6',9"]tercarbazole (Compound V)

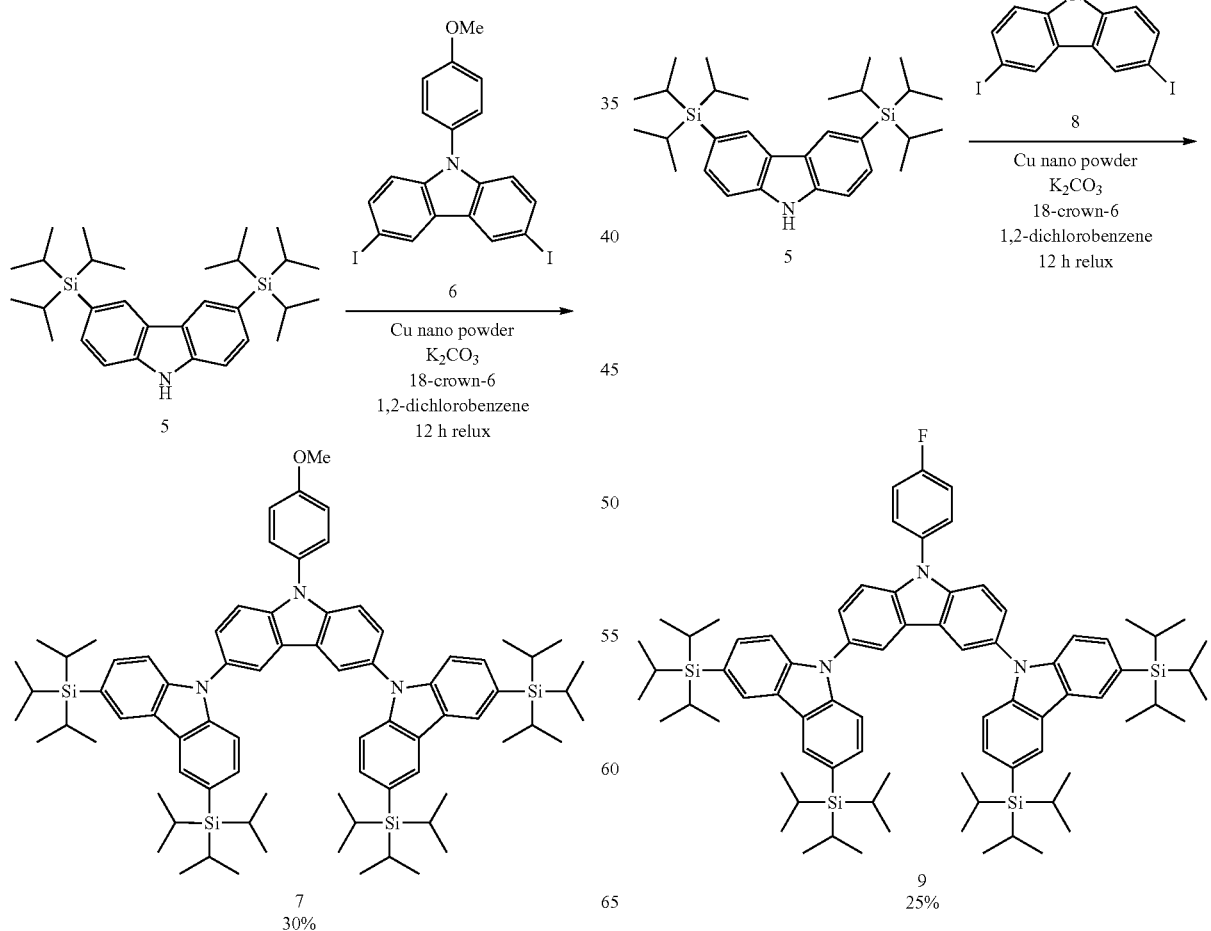

A mixture of 3,6-bis-triisopropylsilanyl-carbazole 5 (10.0 g, 0.021 mol), 3,6-diiodo-9-(4-fluoro-phenyl)-9H-carbazole 8 (4.7 g, 0.01 mol), $K_2CO_3$ (5.8 g, 0.042 mol), Cu nano powder (1.3 g, 0.021 mol), and 18-crown-6 (5.5 g, 0.021 mol) in 1,2-dichlorobenzene was degassed with argon while stirring. The reaction mixture was then refluxed under argon for 12 hours at 178° C. The crude mixture was filtered and the residue was washed with $CH_2Cl_2$. The combined filtrates were concentrated and the residue was purified by chromatography on a 120 g $SiO_2$ column five times with a cyclohexane eluent. Appropriate pure fractions were collected to yield 3.0 g (25%) of white powder of 9'-(4-fluoro-phenyl)-3,6,3",6"-tetrakis-triisopropylsilanyl-9'H-[9,3';6',9"]tercarbazole 9.

Example 3

Synthesis of 9,9-Bis-(4-phenyl-3,6,3",6"-tetrakis-triisopropylsilanyl-9'H-carbazole)-9H-fluorene (Compound IV)

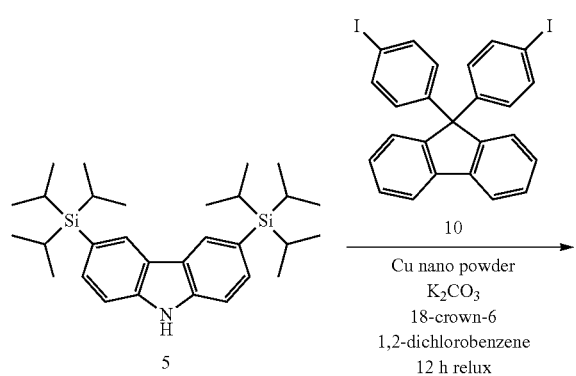

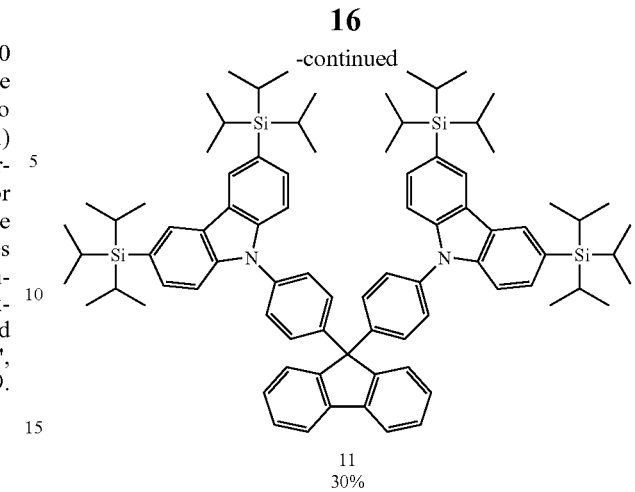

11
30%

A mixture of 3,6-bis-triisopropylsilanyl-carbazole 5 (5.0 g, 0.011 mol), 9,9-bis-(4-iodo-phenyl)-9H-fluorene 10 (2.8 g, 0.005 mol), $K_2CO_3$ (5.8 g, 0.021 mol), Cu nano powder (0.65 g, 0.021 mol), and 18-crown-6 (2.7 g, 0.011 mol) in 50 ml 1,2-dichlorobenzene was degassed with argon while stirring. The reaction mixture was then refluxed under argon for 12 hours at 178° C. The crude mixture was filtered and the residue was washed with $CH_2Cl_2$. The combined filtrates were concentrated and residue was purified by chromatography on a 120 g $SiO_2$ column five times with a cyclohexane eluent at a flow rate of 20 ml/min to yield 1.9 g (30%) of white powder of 9,9-bis-(4-phenyl-3,6,3",6"-tetrakis-triisopropylsilanyl-9'H-carbazole)-9H-fluorene 11.

Example 4

Synthesis of 9,9-Bis-[4-(3-Triisopropylsilylcarbazol)-phenyl]-fluorene (Compound IX)

Scheme 1

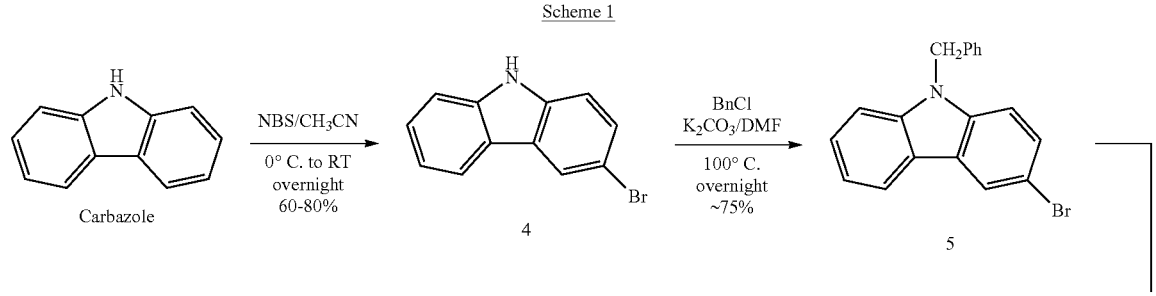

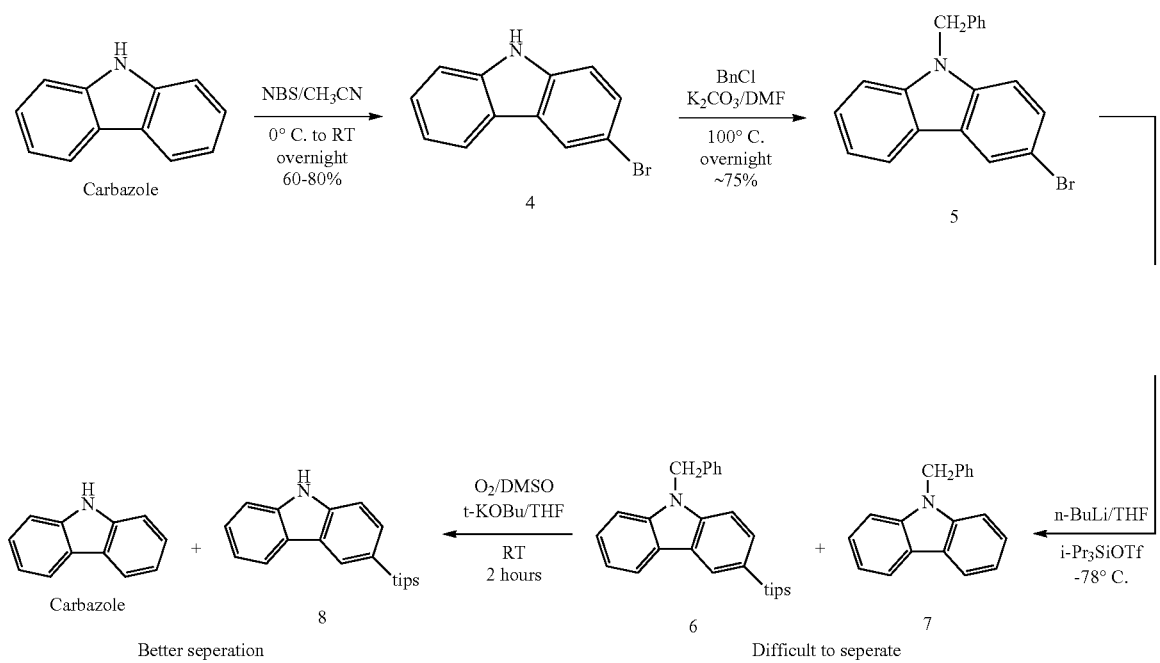

-continued

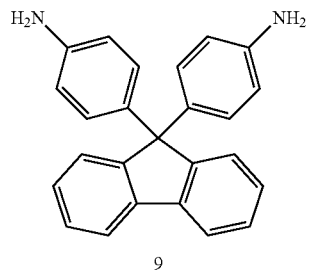
9

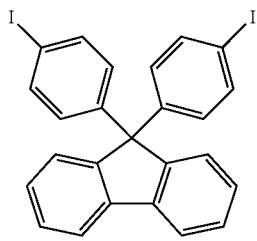
10

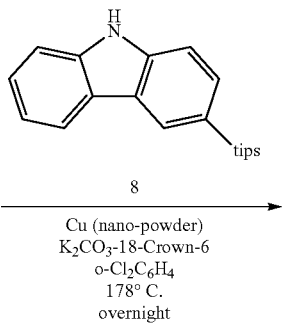
8

NaNO$_2$/HCl/H$_2$O
KI/60° C.
6 hours

Cu (nano-powder)
K$_2$CO$_3$-18-Crown-6
o-Cl$_2$C$_6$H$_4$
178° C.
overnight

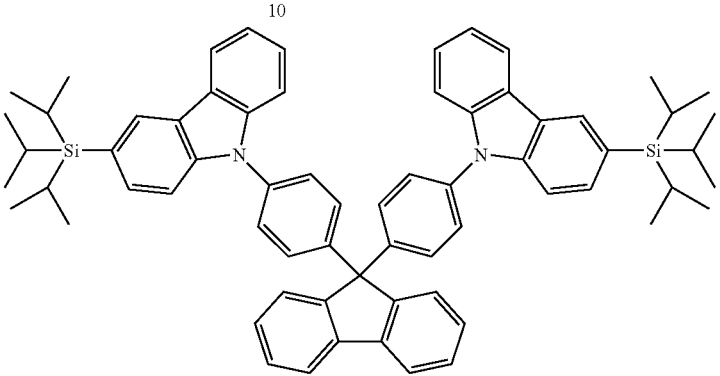
1
30

Synthesis of 3-Bromocarbazole

To a suspension of 9.153 g (54.7 mmol) of carbazole in 100 ml of HPLC grade acetonitrile at 0° C. was slowly added 10.433 g (58.6 mmol) of N-bromosuccinimide (NBS) under vigorous stirring. After the NBS was added, the contents of the flask's were slowly brought to room temperature and stirred overnight. A bulky white precipitate was filtered, washed with cold acetonitrile (2×30 ml) and hexane (2×50 ml), and dried under vacuum to constant weight to yield 7.95 g (59% yield) of 3-bromocarbazole 4 as a fluffy white solid. Additional product can be isolated from the filtrate ($R_f$=0.26 for carbazole and $R_f$=0.16 for 3-bromocarbazole 4 in EtOAc/hexane=85:15).

Synthesis of 9-N-Benzyl-3-bromocarbazole

To a solution of 34.6 g (0.141 mol) of 3-bromocarbazole 4 in 350 ml of anhydrous DMF was added 34.4 g (0.248 mol, 1.77 eq.) of powdered anhydrous potassium carbonate (K$_2$CO$_3$), followed by an addition of 2.05 g (7.75 mmol, ~5.5 mol %) of 18-crown-6 and 18.96 g (0.149 mol) of benzyl chloride at room temperature. The temperature of the mixture was maintained at 100° C., and the mixture was stirred for 23 hours. The mixture was removed from the heat, cooled to ambient temperature, and then the solvent was removed from the mixture on a rotary evaporator under high vacuum. About 1 L of cold water was added to the residue, and the products were extracted with dichloromethane (2×0.5 L). The organic extract was washed with 1 L of water, dried over Na$_2$SO$_4$, and concentrated on a rotary evaporator to yield 50 g of white solid. The crude product containing some unreacted 3-bromocarbazole 4 ($R_f$=0.44 for 5 and $R_f$=0.16 for 4 in CH$_2$Cl$_2$/hexane=2:8) was purified on CombiFlash (2 runs, 330 g column, hexane/dichloromethane) to give 39.4 g (83% yield) of pure 9-N-benzyl-3-bromocarbazole 5 as a white solid.

Synthesis of 9-N-Benzyl-3-triisopropylsilyl-carbazole

A solution of 3.854 g (11.46 mmol) of 9-N-benzyl-3-bromocarbazole 5 in 70 ml of anhydrous THF was cooled to −78° C., and 5.0 ml of n-BuLi (2.5 M/hexane, 12.5 mmol, 1.1 eq.) was slowly added using a syringe at a suitable rate for maintaining a temperature below −74° C. The resulting yellow solution was stirred at −78° C. for 40 minutes, and then neat triisopropylsilyl triflate (TIPS-triflate) was added dropwise to the reaction mixture using a syringe. The reaction mixture was stirred for 30 minutes and was then slowly allowed to warm up to room temperature for a period of two hours. The reaction mixture was quenched with ice water, extracted with ethyl acetate (3×50 ml), and the organic phase was dried over Na$_2$SO$_4$. After concentration on a rotary evaporator, a colorless oil was purified on CombiFlash (120 g column, hexane) to afford 2.55 g of clear oil. Although this material produces one spot on TLC ($R_f$=0.67 in EtOAc/hexane=1:9), a second spot related to the reduced material 7 can be seen in hexane ($R_f$=0.27 for 6 and $R_f$=0.19 for 7). The HPLC results indicated that the oil contained about 60% of the product 9-N-benzyl-3-triisopropylsilyl-carbazole 6. This material was used for the following de-protection step. Only a trace amount (0.115 g) of the pure 9-N-benzyl-3-triisopropylsilyl-carbazole 6 was isolated to confirm the product's structure.

Synthesis of 3-Triisopropylsilyl-carbazole

A. Deprotection of Pure 9-N-Benzyl-3-triisopropylsilyl-carbazole 6

To the suspension of 0.1135 g (0.274 mmol) of pure 9-N-benzyl-3-triisopropylsilyl-carbazole 6 in 4 ml of DMSO was added 2 ml (2 mmol) of a 1 M/THF solution of KOBu-t at room temperature, resulting in the formation of a clear solution. Oxygen was bubbled through the reaction mixture at ~18° C. for 5 minutes, after which the oxygen flow was stopped. The reaction was quenched with ice water (50 ml), extracted with dichloromethane (2×30 ml), and the organic layer was separated and dried over $Na_2SO_4$. The extract was concentrated on a rotary evaporator to give 0.12 g of a yellow solid, which was purified on CombiFlash (4 g column, hexane) to afford 0.08 g (95% yield) of pure 3-triisopropylsilyl-carbazole 8 as a white solid.

B. Deprotection of Mixture of 6 and 7

A total of 1.19 g of crude 6 (~60% content by HPLC, 0.7 g pure 6, 1.72 mmol) from the above reaction of synthesis of 6 was suspended in 2 ml of DMSO. A total of 30 ml (30 mmol) of 1 M/THF solution of KOBu-t was added, and oxygen was bubbled through the solution at ambient temperature until the starting material disappeared, indicated by TLC (at this stage the color of the reaction usually turns orange). As mentioned above, the crude 6 produces only one spot on TLC ($R_f$=0.67 in EtOAc/hexane=1:9). After deprotection, the TLC indicates the presence of four compounds with a major one corresponding to the product 8 and the following $R_f$ values: trace amounts of unreacted 6 with $R_f$=0.67, the major spot of the product 8 with $R_f$=0.37, and two minor spots with $R_f$=0.26 and 0.18 corresponding to carbazole and an unidentified impurity, respectively. The reaction was quenched with ice water (150 mL) and extracted with ethyl acetate (3×50 ml). The combined organic extracts were washed with water (100 ml), brine (30 ml), and dried over $Na_2SO_4$. After concentration on a rotary evaporator, a total of 2.9 g of yellow oil was obtained. This crude product was purified on CombiFlash (80 g column, hexane/dichloromethane as eluent) to give 0.634 g (89% yield based on 6) of pure deprotected compound 8 as a white solid.

Synthesis of 9,9-Bis-(4-Iodophenyl)-fluorene

A total of 25.5 g (73.18 mmol) of 9,9-bis(4-aminophenyl) fluorene from TCI (Japan) was dissolved in a mixture of 250 ml of water and 45 ml (0.456 mol, 6 eq.) of concentrated HCl. This mixture was placed in a 1 L three-neck round bottom flask equipped with an overhead stirrer, a thermocouple, an addition funnel, and a cooling ice/methanol bath. The flask's contents were cooled to 0° C., and a cold solution of $NaNO_2$ (10.6 g, 153.6 mmol, 2 eq.) in 40 ml of water was added dropwise to the solution under vigorous stirring. The resulting yellow solution was further stirred at 0° C. for 30 minutes. This solution was transferred to a jacketed addition funnel with a jacket filled with ice in order to maintain the prepared diazonium salt at a temperature of 0° C. A solution of this salt was slowly added to a solution of KI (48.3 g, 0.291 mol, 4 eq.) in 250 ml of water at ~10° C. under vigorous stirring. After completing the addition, the resulting dark mixture was maintained at a temperature of 60° C. and stirred for 6 hours. The mixture was cooled to room temperature, and the organic material was extracted with dichloromethane (3×0.5 L), washed with water (1 L), dried over $Na_2SO_4$, and concentrated on a rotary evaporator to give 45 g of black foam. This crude material was purified on CombiFlash (330 g column, hexane) to give 24.7 g (59% yield) of 9,9-bis-(4-iodophenyl)-fluorene 10 as a white solid with $R_f$=0.33 (in hexane).

Synthesis of 9,9-Bis-[4-(3-Triisopropylsilylcarbazol)-phenyl]-fluorene

A mixture of 1.7585 g (3.08 mmol) of 10, 2.1678 g (6.699 mmol, 2.17 eq.) of 8, 2.9422 g (21.28 mmol, 3.18 eq. based on 8) of anhydrous $K_2CO_3$, 0.3220 g (1.21 mmol, 18 mol % based on 8) of 18-crown-6, and 0.9715 g (15.2 mmol, 2.26 eq. based on 8) of nano-powdered copper in 110 ml of anhydrous o-dichlorobenzene was charged under an argon blanket into a 0.5 L flask, equipped with a magnetic stirrer, thermocouple, condenser, heating mantle, and argon-filled balloon. The mixture was maintained at a temperature of 177° C. and stirred for 40 hours. The reaction was monitored by TLC and HPLC. After about two days when the reaction was complete, the mixture was cooled to room temperature and quenched with water (0.5 L). The organic products were extracted with dichloromethane (2×100 ml), dried over $Na_2SO_4$, and concentrated on a rotary evaporator. o-Dichlorobenzene from the residue was removed under high vacuum to give 5.2 g of viscous brown oil. This material was purified on CombiFlash (120 g, hexane/dichloromethane), and 1.72 g (47% yield) of 9,9-bis-[4-(3-triisopropylsilylcarbazol)-phenyl]-fluorene 1 was isolated as a white foam. Concentration of the mixed fractions afforded 1.12 g of impure product contaminated with 8. The pure material (1.72 g) was dissolved in a minimum amount of warm dichloromethane (~15 ml), diluted with warm hexane (~80 ml), and slowly concentrated on a rotary evaporator at room temperature until the volume of the reaction mixture was about one-third of the original volume. Upon the cooling of the residue in an ice bath, product 1 slowly crystallized. The precipitate was filtered, washed quickly with cold hexane (2×20 ml), and dried under vacuum until constant weight to give 1.35 g of 1 as a white solid (lot A352-79-1). Calculated for $C_{67}H_{72}N_2Si_2$ 0.5 mol hexane: C, 83.69; H, 7.93; N, 2.79. Found: C, 83.94; H, 7.97; N 2.81. HPLC purity 99.7%.

Example 5

Synthesis of 9-N-(4-methoxy-phenyl)-3,6-Bis-[(3-Triisopropylsilylcarbazolyl)]carbazole[2] (Compound VII) and 9-N-(4-Fluoro-phenyl)-3,6-Bis-[(3-Triisopropylsilylcarbazolyl)]carbazole[3] (Compound VIII)

Scheme 2

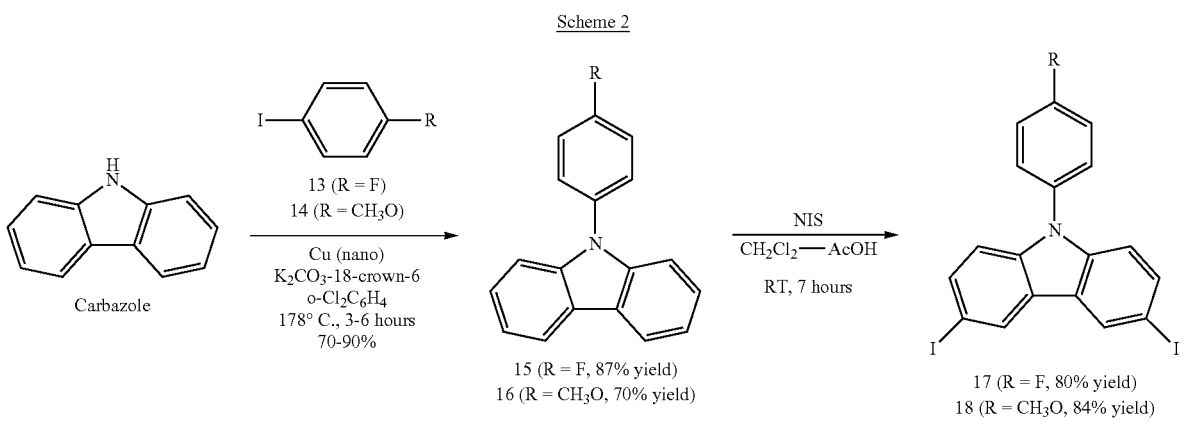

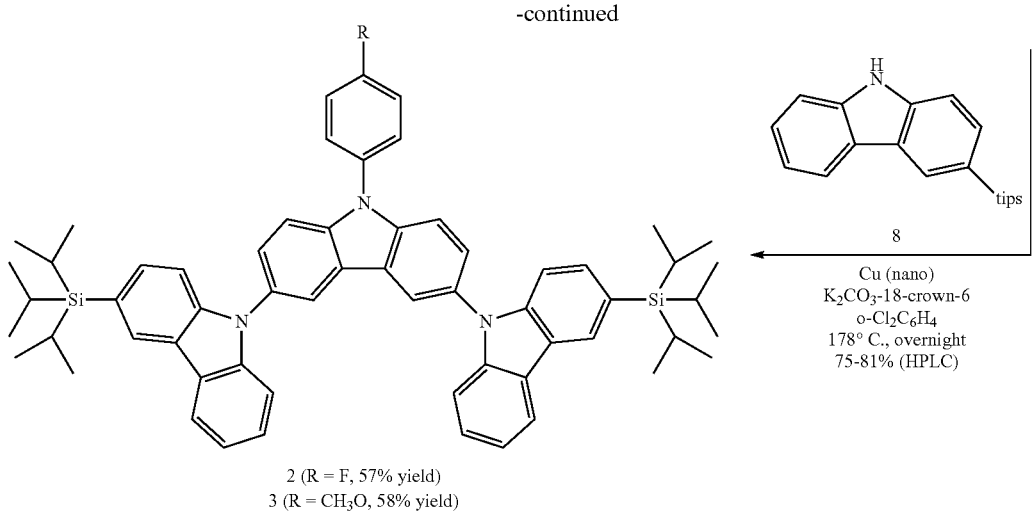

2 (R = F, 57% yield)
3 (R = CH₃O, 58% yield)

As depicted in Scheme 2 above, compounds VII and VIII were synthesized similarly to compound IX.

The coupling of carbazole with commercially available 4-fluoro-iodobenzene 13 and 4-methoxy-iodobenzene 14 smoothly occurred in the presence of nano-copper under conditions described in Scheme 1 for the synthesis of compound IX (1) from 10. The iodination of 15 and 16 using N-iodosuccinimide (NIS) under acidic conditions (Maruyama et al., "Synthesis of novel carbazolylacetylene-derived macrocycles". *Synthesis*, 12: 1794-1799 (2001)) resulted in the formation of 3,6-diiodosubstituted carbazoles 17 and 18 in good yield. A copper-mediated coupling of diiodides 17 and 18 with triisopropylsilyl(TIPS)-carbazole 8 easily provides target compounds 2 and 3 (compounds VIII and VII).

Synthesis of 9-N-(4-Fluorophenyl)-carbazole

A mixture of 10.41 g of 95% carbazole (9.89 g, 59.1 mmol), 15.44 g (69.5 mmol, 1.17 eq.) of 4-iodofluorobenzene (Aldrich), 13.13 g (95 mmol, 1.6 eq.) of anhydrous $K_2CO_3$, 3.11 g (11.76 mmol, ~20 mol %) of 18-crown-6, and 4.22 g (66.41 mmol, 1.1 eq.) of nano-powdered copper in 120 ml of anhydrous o-dichlorobenzene was charged under an argon blanket into a 0.5 L flask, equipped with a magnetic stirrer, a thermocouple, a condenser, a heating mantle, and an argon-filled balloon. The mixture was maintained at a temperature of 177° C. and stirred until the reaction was completed. The reaction was monitored by TLC. After the reaction was complete (i.e., after about 6 hours), the mixture was cooled to room temperature and quenched with 1 L of water. In order to improve the separation of the organic layer, the fluffy black copper residue was optionally removed via filtration through cotton. The organic products were extracted with dichloromethane (2×100 ml), dried over $Na_2SO_4$, and concentrated on a rotary evaporator, following the removal of o-dichlorobenzene under high vacuum. A total of 22 g of brown solid was obtained. This crude material was purified on CombiFlash (330 g column, hexane/dichloromethane, two runs), resulting in the isolation of 14.13 g (87% yield) of pure 9-N-(4-fluorophenyl)-carbazole 15 as a white solid.

Synthesis of 9-N-(4-Methoxyrophenyl)-carbazole

A mixture of 8.76 g of 95% carbazole (8.32 g, 49.7 mmol), 12.91 g (55.1 mmol, 1.1 eq.) of 4-iodoanisole (Aldrich), 10.54 g (76.26 mmol, 1.53 eq.) of anhydrous $K_2CO_3$, 2.04 g (7.71 mmol, ~15 mol %) of 18-crown-6, and 6.45 g (101.5 mmol, 2.0 eq.) of nano-powdered copper in 100 ml of anhydrous o-dichlorobenzene was charged under an argon blanket into a 0.5 L flask, equipped with a magnetic stirrer, a thermocouple, a condenser, a heating mantle, and a balloon filled with argon. The mixture was maintained at a temperature of 178° C. and stirred until the reaction was completed. The reaction was monitored by TLC. After the reaction was complete (i.e., after about 4 hours) by TLC ($R_f$=0.22 for carbazole, $R_f$=0.49 for 4-iodoiniasole and 0.4 for 16 in EtOAc/hexane=1:9), the mixture was cooled to room temperature and quenched with 1 L of water. In order to improve the separation of the organic layer, the fluffy black copper residue was removed via filtration through cotton. The organic products were extracted with dichloromethane (2×100 ml), dried over $Na_2SO_4$, and concentrated on a rotary evaporator, following the removal of o-dichlorobenzene under high vacuum. A total of 23.4 g of brown solid was obtained. This crude material was purified on CombiFlash (330 g column, hexane/dichloromethane), resulting in the isolation of 10.2 g of a white solid. This material was dissolved in ~30 ml of dichloromethane, diluted with hexane (~100 ml), and slowly concentrated on a rotary evaporator at room temperature until about 20% of the original volume was left in the flask. A white solid began to precipitate from the residue upon cooling in ice. The precipitate was filtered, washed with cold hexane (2×30 ml), and dried under vacuum to constant weight to give 9.93 g (70% yield) of pure 9-N-(4-methoxyrophenyl)-carbazole 16 as a white solid.

Synthesis of 9-N-(4-Fluorophenyl)-3,6-diiodocarbazole

A solution of 5.634 g (21.54 mmol) of 15 in a mixture of 130 ml of dichloromethane and 45 ml of glacial acetic acid was placed in a 0.5 L flask, equipped with a magnetic stirrer, a thermocouple, a condenser, an ice bath, and a balloon filled with argon. The mixture was cooled to 10° C., and 10.861 g of 95% solid N-iodosuccinimide (NIS, 10.317 g, 45.85 mmol, 2.1 eq.) was slowly added portion wise to the solution within 10 minutes. After the addition was complete, the reaction was allowed to warm to room temperature and stirred for an additional 6 hours. The solvents ($CH_2Cl_2$ and AcOH) were removed under reduced pressure on a rotary evaporator, 300 ml of dichloromethane was then added to the residue, and the reaction mixture was washed with 10% aqueous KOH (3×200 ml). The products were extracted with dichloromethane, and the organic layer was washed with water (300 ml) and dried over $Na_2SO_4$. The resulting clear yellow solution was concentrated on a rotary evaporator, and the residue was dissolved in ~100 ml of hot dichloromethane. About 300 ml of hexane was added quickly to the solution of product in dichloromethane, and upon cooling the product crystallized. The precipitated solid was filtered, washed with cold hexane (2×30 ml), and dried until constant weight to give 8.84 g (80% yield) of pure 9-N-(4-fluorophenyl)-3,6-diiodocarbazole 17 as a white solid.

Synthesis of 9-N-(4-Methoxyphenyl)-3,6-diiodocarbazole

A solution of 3.95 g (14.45 mmol) of 16 in a mixture of 100 ml of dichloromethane and 35 ml of glacial acetic acid was placed in a 0.5 L flask, equipped with a magnetic stirrer, a thermocouple, a condenser, an ice bath, and a balloon filled with argon. The mixture was cooled to 10° C., and 7.29 g of 95% solid N-iodosuccinimide (NIS, 6.92 g, 30.78 mmol, 2.1 eq.) was slowly added portion wise to the solution within 10 minutes. After the addition was complete, the reaction was allowed to warm to room temperature and was stirred for an additional 6 hours. The solvents ($CH_2Cl_2$ and AcOH) were removed under reduced pressure on a rotary evaporator, 200 ml of dichloromethane was then added to the residue, and the reaction mixture was washed with 10% aqueous KOH (3×100 ml). The products were extracted with dichloromethane, and the organic layer was washed with water (200 ml) and dried over $Na_2SO_4$. The clear yellow solution was concentrated on a rotary evaporator, and the resulting off-white solid residue was dissolved in ~40 ml of hot dichloromethane. About 800 ml of hexane was quickly added to the solution, and the product slowly crystallized overnight upon cooling in the refrigerator. The precipitated solid was filtered, washed with cold hexane (2×30 ml), and dried until constant weight to give 6.34 g (84% yield) of pure 9-N-(4-methoxyphenyl)-3,6-diiodocarbazole 18 as a white solid.

Synthesis of 9-N-(4-Fluoro-phenyl)-3,6-Bis-[(3-Triisopropylsilylcarbazolyl)]carbazole (Compound VIII)

A mixture of 2.2013 g (4.29 mmol) of 17, 2.7620 g (8.53 mmol, 1.99 eq.) of 8 (from Example 4), 3.995 g (28.9 mmol, 3.39 eq. based on 8) of anhydrous $K_2CO_3$, 0.4950 g (1.87 mmol, 22 mol % based on 8) of 18-crown-6, and 1.1920 g (18.75 mmol, 2 eq. based on 8) of nano-powdered copper in 100 ml of anhydrous o-dichlorobenzene was charged under an argon blanket into a 0.5 L flask, equipped with a magnetic stirrer, a thermocouple, a condenser, a heating mantle, and a balloon filled with argon. The mixture was maintained at a temperature of 177° C. and stirred for 40 hours. The reaction was monitored by TLC and HPLC. After about two days, when the reaction was complete, the mixture was cooled to room temperature and quenched with water (0.5 L). The organic products were extracted with dichloromethane (2×100 ml), filtered through loose cotton in order to remove the fluffy copper residue, and dried over $Na_2SO_4$. Concentration of the reaction mixture on a rotary evaporator and the following removal of o-dichlorobenzene under high vacuum provided 6.1 g of brown oil. This material was purified on CombiFlash (330 g, hexane/dichloromethane), resulting in a white solid. This material was dissolved in a minimum amount of warm dichloromethane (~15 ml), diluted with warm hexane (~150 ml), and slowly concentrated on a rotary evaporator at room temperature until crystallization occurred. The obtained suspension was cooled on an ice bath, filtered, and the filter cake was then washed with cold hexane (2×20 ml). The solid product was dried under vacuum to constant weight to yield 2.21 g (57% yield) of pure compound VIII as a white solid (lot A352-105-2) with HPLC purity 100%.

Calculated for $C_{60}H_{66}FN_3Si_2 \cdot 0.2$ mol $H_2O$: C, 79.37; H, 7.37; N, 4.63.

Found: C, 79.36; H, 7.54; N, 4.61.

Synthesis of 9-N-(4-Methoxy-phenyl)-3,6-Bis-[(3-Triisopropylsilylcarbazolyl)]carbazole (Compound VII)

A mixture of 1.6183 g (3.08 mmol) of 18, 2.0492 g (6.33 mmol, 2 eq.) of 8, 2.9110 g (21.06 mmol, 3.3 eq. based on 8) of anhydrous $K_2CO_3$, 0.486 g (1.83 mmol, 29 mol % based on 8) of 18-crown-6, and 1.189 g (18.71 mmol, 2.95 eq. based on 8) of nano-powdered copper in 100 ml of anhydrous o-dichlorobenzene were charged under an argon blanket into a 0.5 L flask, equipped with a magnetic stirrer, a thermocouple, a condenser, a heating mantle, and a balloon filled with argon. The mixture was maintained at a temperature of 177° C. and stirred for 40 hours. The reaction was monitored by TLC and HPLC. After about two days, when reaction was complete, the mixture was cooled to room temperature and quenched with water (0.5 L). The organic products were extracted with dichloromethane (2×100 ml), filtered through loose cotton in order to remove fluffy copper residue and dried over $Na_2SO_4$. Concentration of the reaction mixture on a rotary evaporator and the following removal of o-dichlorobenzene under high vacuum provided 6.2 g of dark oil. This material was purified on CombiFlash (330 g, hexane/dichloromethane), resulting in 3.2 g of yellow oil. This material was re-purified one more time on CombiFlash (120 g column, hexane/dichloromethane) to provide 2.3 g of clear yellow oil by TLC. This oil was dissolved in hexane (~20 ml) and left in the refrigerator overnight. The precipitated fluffy solid was filtered using a 0.45 PTFE membrane filter, quickly washed with cold hexane (2×15 ml), and dried over nitrogen first, followed by drying under high vacuum until constant weight. Compound VII was obtained as a light-sensitive white solid (1.61 g, 57% yield) which must be kept in the dark (lot A352-107-2) with HPLC purity 99%-F. Calculated for $C_{61}H_{69}N_3OSi_2 \cdot 0.2$ mol $H_2O$: C, 79.64; H, 7.60; N, 4.57. Found: C, 79.70; H, 7.85; N, 4.58.

Example 6

Measurement of Absorbance and Photoluminescence

The UV-visible absorption spectra were recorded on a SHIMADZU UV-3101 PC double beam spectrophotometer. The photoluminescence studies were conducted with a HORIBA JOBIN YVON Fluoromax-4 P spectrofluorimeter on $10^{-5}$ M solutions of the different hosts ($\lambda_{exc}$: 300 nm). The emission measurements at 77° K were performed using the FL-2013 Dewar liquid nitrogen assembly from HORIBA JOBIN YVON. Toluene and dichloromethane (DCM) were spectrometric grade and 2-methyltetrahydrofuran was ≥99.0% (anhydrous).

Figure 2:
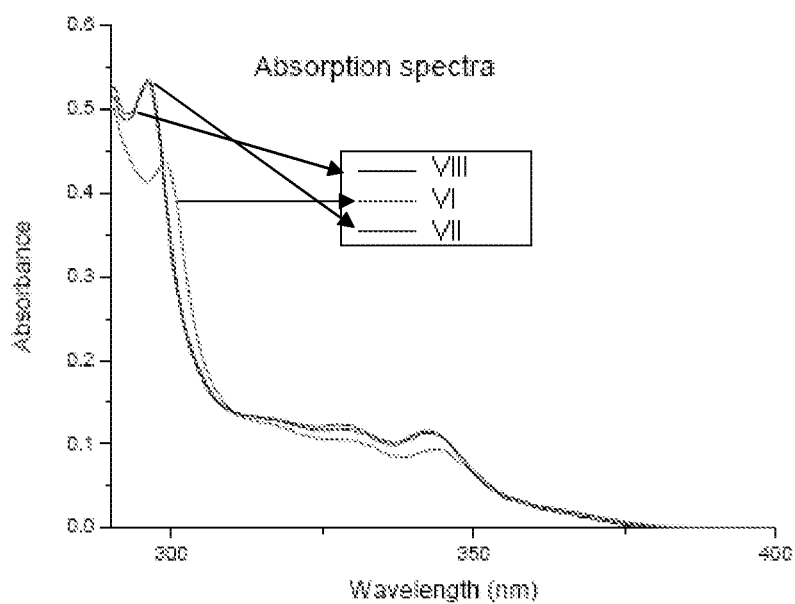
FIG. 2 shows the UV-vis absorption spectra of compounds represented by Formulae VI, VII, and VIII.
Figure 3:
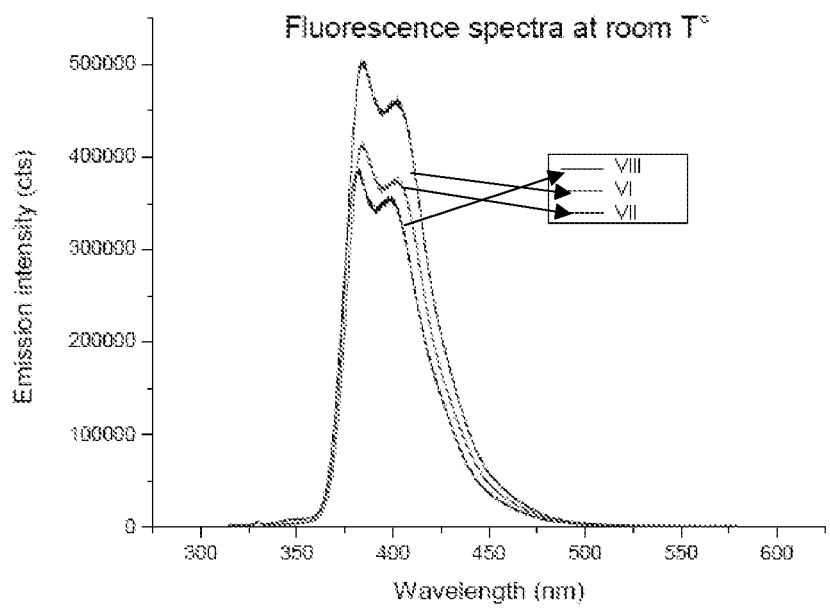
FIG. 3 shows the fluorescence spectra of compounds represented by Formulae VI, VII, and VIII.
Figure 4:
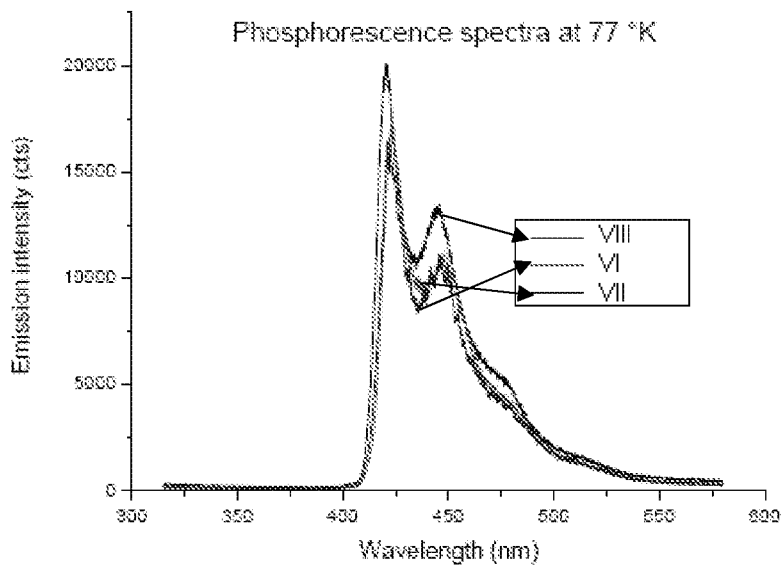
FIG. 4 shows the emission spectra of compounds represented by Formulae VI, VII, and VIII.

As shown in FIGS. 2-4, the carbazole-based compounds of the present invention have a triplet-energy-gap which is below that of phosphorescent blue emitters (i.e., approximately 455 nm).

Example 7

Measurement of Cyclic Voltammetry

Cyclic voltammetry experiments were performed using a METROHM VA Trace Analyzer 746 in conjunction with a VA Stand 747 measuring unit. All measurements were carried out at room temperature under inert atmosphere with a conventional three-electrode configuration, where the solution was degassed before use with a stream of argon for 5-10 min. The working electrode was a glassy carbon disk, while the counter electrode was a Pt wire. The reference electrode was an Ag/AgCl reference electrode filled with a KCl saturated solution in methanol or a pseudo-reference Pt wire.

Figure 5:
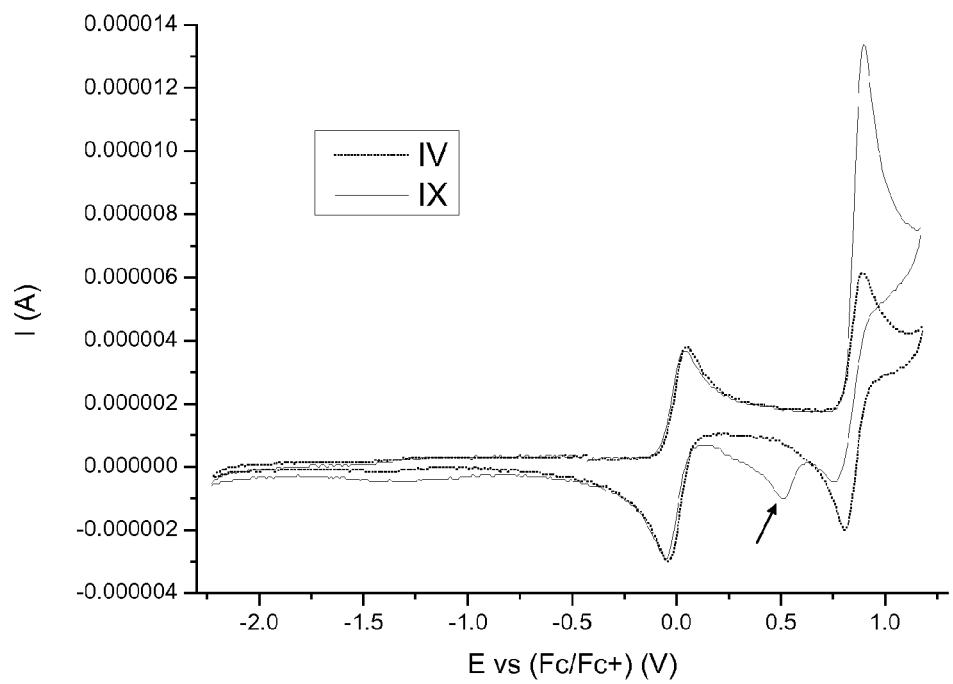
FIG. 5 shows cyclic voltammetry curves of compounds represented by Formulae IV and IX.

As shown in FIG. 5 the carbazole-based compound IV of the present invention has a reversible first oxidation wave and compound IX has a non-reversible first oxidation wave (arrow pointed).

Figure 6:
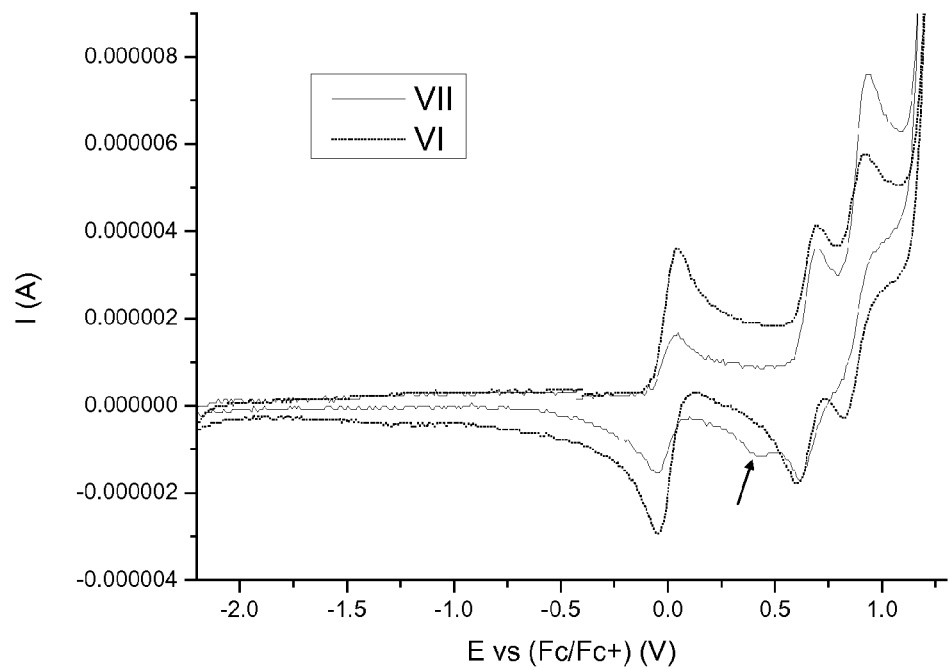
FIG. 6 shows cyclic voltammetry curves of compounds represented by Formulae VI and VII.
Figure 7:
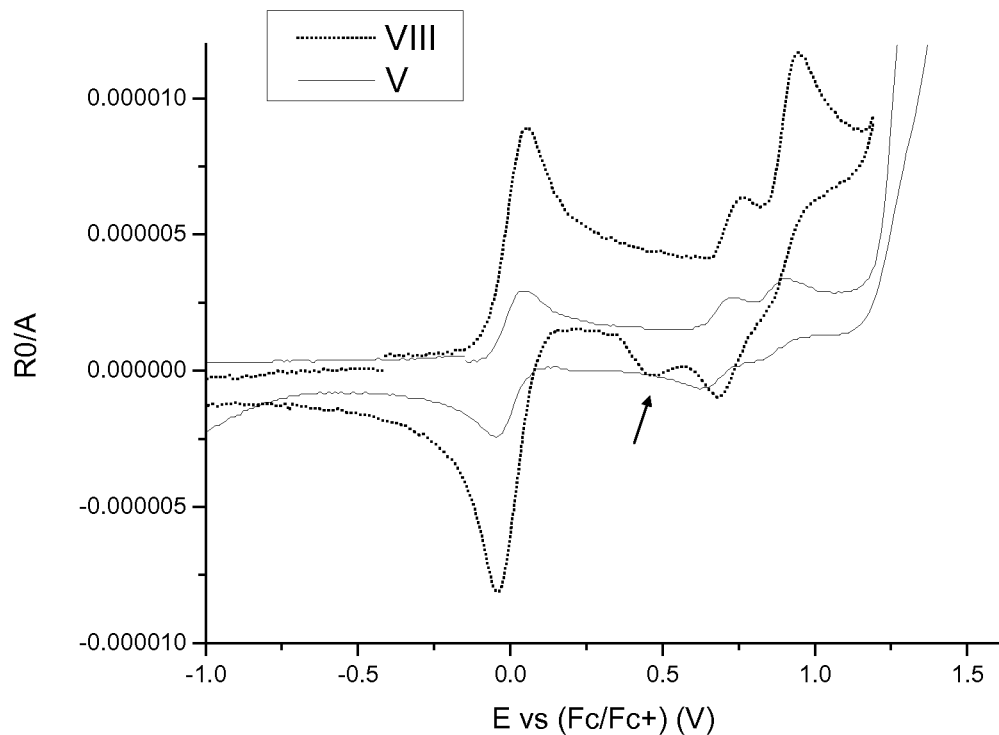
FIG. 7 shows cyclic voltammetry curves of compounds represented by Formulae VIII and V.

As shown in FIGS. 6 and 7 the carbazole-based compounds VII and VIII of the present invention have a reversible first oxidation wave and a non-reversible second oxidation wave (arrow pointed) and the compounds VI and V have two reversible oxidation waves.

Since reversible oxidation waves in cyclic voltammetry are an indication of improved electrochemical stability, FIGS. 5-7 show that the more the substituted carbazole compounds of the invention are bearing trialkylsilyl substituents, the more electrochemical stable they are.

| Compd. | Solvent | Absorption $\lambda$ max (nm) | | | | | | $\lambda$ onset (nm) | $E_g$ (eV) | Fluorescence T° | $\lambda$ (nm) | | |
|---|---|---|---|---|---|---|---|---|---|---|---|---|---|
| IX | DCM | 266 | 289 | 296 | 310 | 328 | 342 | | | RT | 349 | 365 | 383 |
|  | 2-methyl-THF | 266 | 289 | 296 | 310 | 328 | 342 | 353 | 3.51 | RT | 349 | 365 | 380 |
| IV | 2-methyl-THF | 270 | 289 | 299 | 310 | 328 | 342 | 353 | 3.51 | RT | 349 | 365 | 380 |
| VII | 2-methyl-THF | 268 | 287(sh) | 296 | 314(sh) | 328 | 343 | 381 | 3.25 | RT | 384 | 402 | |
|  |  |  |  |  |  |  |  |  |  | 77° K | 377 | 398 | +phospho |
| VI | 2-methyl-THF | 271 | 288(sh) | 298 | 315(sh) | 328 | 343 | 381 | 3.25 | RT | 384 | 402 | |
|  |  |  |  |  |  |  |  |  |  | 77° K | 376 | 397 | phospho |
| VIII | 2-methyl-THF | 267 | 288(sh) | 296 | 314(sh) | 328 | 343 | 381 | 3.25 | RT | 382 | 399 | |
|  |  |  |  |  |  |  |  |  |  | 77° K | 374 | 394 | +phospho |
| V | 2-methyl-THF | 271 | 289(sh) | 299 | | 327 | 343 | 381 | 3.25 | RT | 382 | 399 | |
|  |  |  |  |  |  |  |  |  |  | 77° K | 373 | 392 | +phospho |

| Compd. | Solvent | Phosphorescence $\lambda$ (nm) | | | | | | | | $E_T$ (ev) |
|---|---|---|---|---|---|---|---|---|---|---|
| IX | DCM | | | | | | | | | |
|  | 2-methyl-THF | 429 | 436 | 452 | 462 | 471 | 487 | 497 | 527 | 2.89 |
| IV | 2-methyl-THF | 430 | 437 | 453 | 462 | 471 | 487 | 497 | 527 | 2.88 |
| VII | 2-methyl-THF | 423 | 448 | 477(sh) | | | | | | 2.93 |
| VI | 2-methyl-THF | 422 | 446 | 477(sh) | | | | | | 2.94 |
| VIII | 2-methyl-THF | 420 | 445 | 477(sh) | | | | | | 2.95 |
| V | 2-methyl-THF | 420 | 443 | 475(sh) | | | | | | 2.95 |

The solvent in all of the experiments was anhydrous dichloromethane and the supporting electrolyte was 0.1 M tetrabutylammonium hexafluorophosphate. Host concentrations were 0.5-2 mM. The scan rate was fixed to 100 or 500 my/s. Ferrocene was used as an internal reference to determine the oxidation potential of the hosts.

As described above, the energy of the lowest excited triplet state of the carbazole-based compounds of the present invention should be higher in energy than the lowest emitting state of the phosphorescent emitter. In some embodiments, the triplet energy of the carbazole-based compounds of the present invention may be at least 2.725 eV so that the compounds can host blue phosphorescent emitters, allowing the host to be used with phosphorescent emitters emitting blue light of 455 nm (2.725 eV). As shown in the table below, all of compounds IV, V, and VI have triplet energies of more than 2.725 eV, making them promising compounds as host materials for blue emission.

Example 8

Blue Hosts Sublimation

For sublimation, a Creaphys tube-based Vacuum Sublimation Unit DSU05-v was used. An external oven with 3 independent heating zones creates a temperature gradient inside the glass tube that is intended for the deposition of the compounds.

The sublimation unit provides the ability to purify organic volatile compounds by vacuum sublimation, both for sublimable compounds and liquid phase compounds.

The collected fractions were analyzed on HPLC or NMR to determine their purity. After sublimation, the compounds were stored away from air and light.

| Structure | Mass mg | Time Min | Yield* % | Purity % |
|---|---|---|---|---|
| 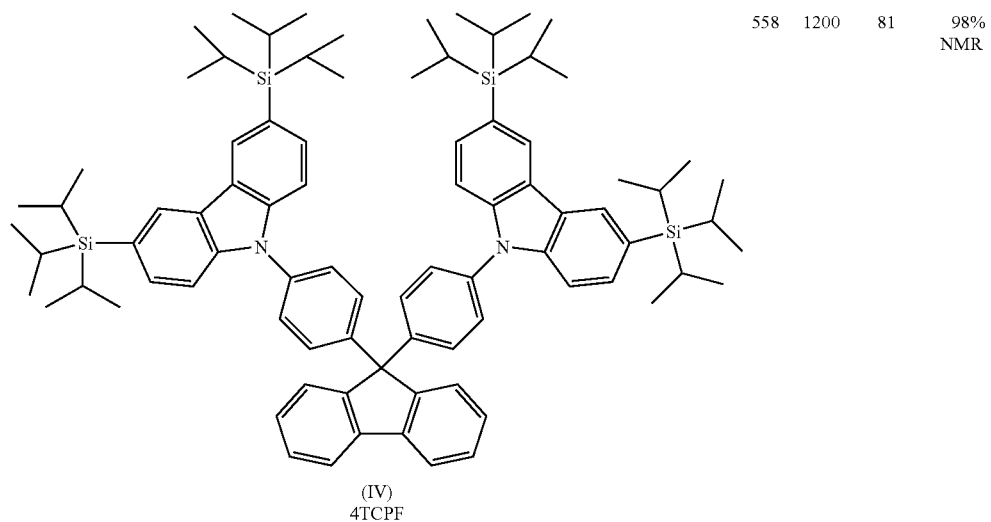<br>(IV)<br>4TCPF | 558 | 1200 | 81 | 98% NMR |
| 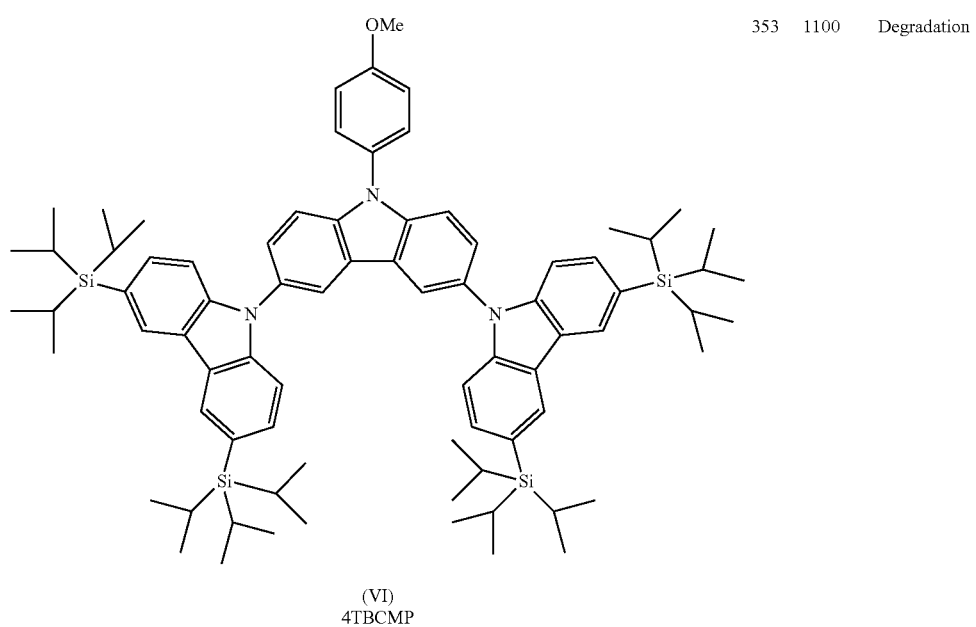<br>(VI)<br>4TBCMP | 353 | 1100 | Degradation | |

| Structure | Mass mg | Time Min | Yield* % | Purity % |
|---|---|---|---|---|
| 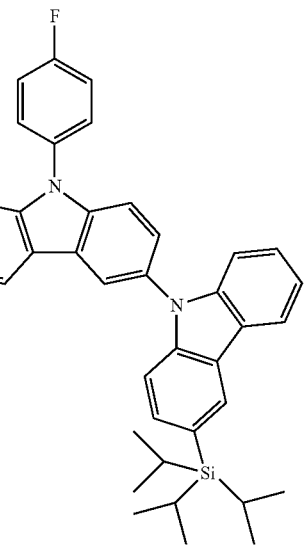<br>(VIII)<br>2TBCFP | 330 | 1335 | 78 | 99.7% HPLC |
| 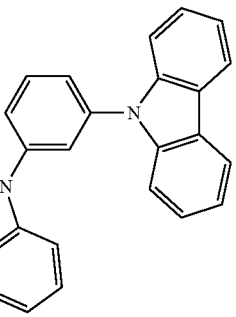<br>(mCp, comparative example) | 4235 | 750 | 75 | 99.7% HPLC |
| 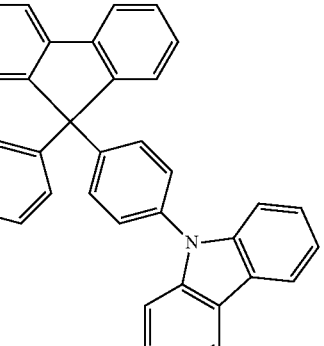<br>(CPF, comparative example) | 4670 | 362 | 82 | —** |
*yield of recovered good product,
**insoluble

Example 9

Measurement of Glass Transition Temperature (Tg)

For glass transition temperature (Tg) determinations, measurements were performed on a TA 2920 (TA Instruments) or a DSC 823 (Mettler-Toledo). The typical specimen weight ranges were between 10 mg to 20 mg, depending on sample characteristics. The temperature program included two heating and one cooling steps, at 20 K/min. The choice of the upper temperature depended on sample characteristics, mainly thermal stability and degree of crystallinity. The glass transition was characterized by $T_g$: intersection with the median line between the two extrapolated baselines. Measurements were repeated at least twice, depending on the amount of available material.

As show in the table below, the compounds IV has a notable higher Tg value than the comparative example CPF and the compound V has a notable higher Tg value than the compound VIII. Surprisingly, the trialkylsilyl substituted carbazoles compounds of this invention are all the more thermically stable as they are bearing more trialkylsilyl substituents.

|     | Tg (° C.) |
| --- | --- |
| IV  | 211 |
| CPF | 165 * |
| VIII | 174 |
| V   | 215 |

* litterature value

Example 10

Solubility Tests

The solubility tests were carried out at 20° C. by adding 1 ml of solvent to the suitable amount of compound powder in a sampling vial and under magnetic stirring.

As shown in the solubility measurement results in the table below, the compounds of Formulae IV to IX have good solubilities toward chlorobenzene and toluene, while the control compound (CPF) lacks solubility for most organic solvents.

| Chlorobenzene | |
| --- | --- |
| Comparative example(CPF) | 1.24 mg/ml < S < 2.96 mg/ml (1.9 mmol/l < S < 4.6 mmol/l) |
| Formula IX | S > 57 mg/ml (59 mmol/l) |
| Formula IV | S > 54 mg/ml (42 mmol/l) |
| Formula VII | S > 56 mg/ml (62 mmol/l) |
| Formula VI | S > 55 mg/ml (45 mmol/l) |
| Formula VIII | S > 51 mg/ml (57 mmol/l) |
| Toluene | |
| Formula IX | S > 47 (mg/ml) (49 mmol/l) |
| Formula IV | S > 39 (mg/ml) (31 mmol/l) |

The carbazole-based compounds having suitable substituents, in particular, the triisopropylsilyl group of the present invention, have been found to be promising for large-scale light emitting diodes since they allow for solvent-processing techniques, such as spin-coating, (ink-jet) printing processes, high concentration demanding printing processes (roll to roll, flexography, etc), etc., while maintaining the other necessary properties for OLED devices.

Example 11

OLED Devices

Figure 8:
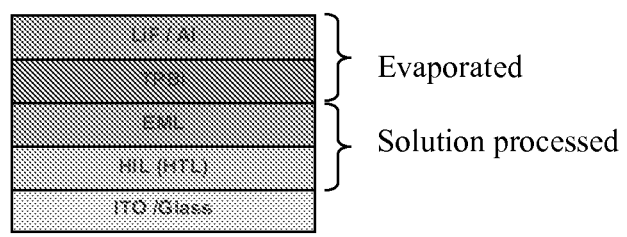
FIG. 8 describes the general structure used to fabricate OLED devices for host molecules testing.

A general structure as shown in FIG. 8 was used to fabricate OLED devices having an emissive layer (EML) containing the carbazole based host materials VIII and V of the present invention.

A reference OLED device based on PVK as a host was fabricated to benchmark the performance of the carbazole based compounds of the present invention. Keeping the OLED structure identical, devices based on VIII and V were fabricated to compare performance with PVK. Apart from the host, the EML comprises an electron transporter (OXD7) to achieve charge balance and FIrpic as a blue phosphorescent emitter. The EML composition was identical in all three devices: Host/OXD7/FIrpic=60:30:10 in weight.

Device fabrication was done as below: a HIL based on polyethylenedioxythiophene:polystyrene sulphonate (CH8000 form HC Stack) was deposited by spin coating on indium tin oxide (ITO) coated glass substrates to a thickness of 60 nm. The obtained film was dried on a hot plate at 200° C. for 10 min. The emissive layer was obtained by spincoating a Host: OXD7: Firpic formulation in toluene. The total solid content was 1.5 wt %. Such formulation was deposited on top of the HIL to a thickness of 70 nm and subsequently dried on a hot plate at 80° C. for 10 min. An 30 nm thick ETL, namely 2,2',2"-(1,3,5-benzenetriyl)-tris(1-phenyl-1-H-benzimidazole) (TPBi, purchased from Lumtec) was deposited by vacuum deposition onto the EML at a rate of 2 Å/s. Finally cathode layers comprising 1 nm of LiF and 100 nm of Al were deposited by thermal evaporation at a rate of 0.1 and 2 Å/s respectively.

Electronic and photometric characterizations were done with a Hamamatsu C9920-12 measurement system coupled to a Keithley 2400 source measure unit. All device fabrication and characterization steps after PEDOT spinning were carried out in an inert atmosphere.

Figure 9:
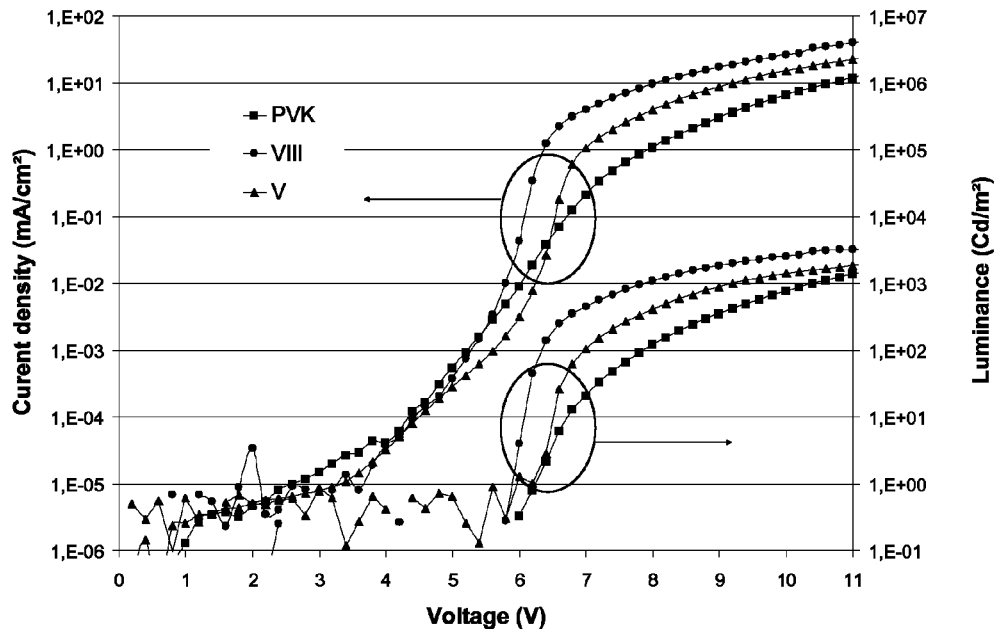
FIG. 9 shows the Intensity-Voltage-Luminance (IVL) curves of three OLED devices containing the compounds represented by formulae VIII and V versus reference material PVK (poly vinyl carbazole).

FIG. 9 shows IVL characteristics of the two OLED devices containing compounds VIII and V which have higher current density and luminance than the PVK reference device. This can be attributed to better hole injection and/or transport with VIII and V versus PVK. This better performance can be attributed to the higher content of inert trialkylsilyl groups.

Figure 10:
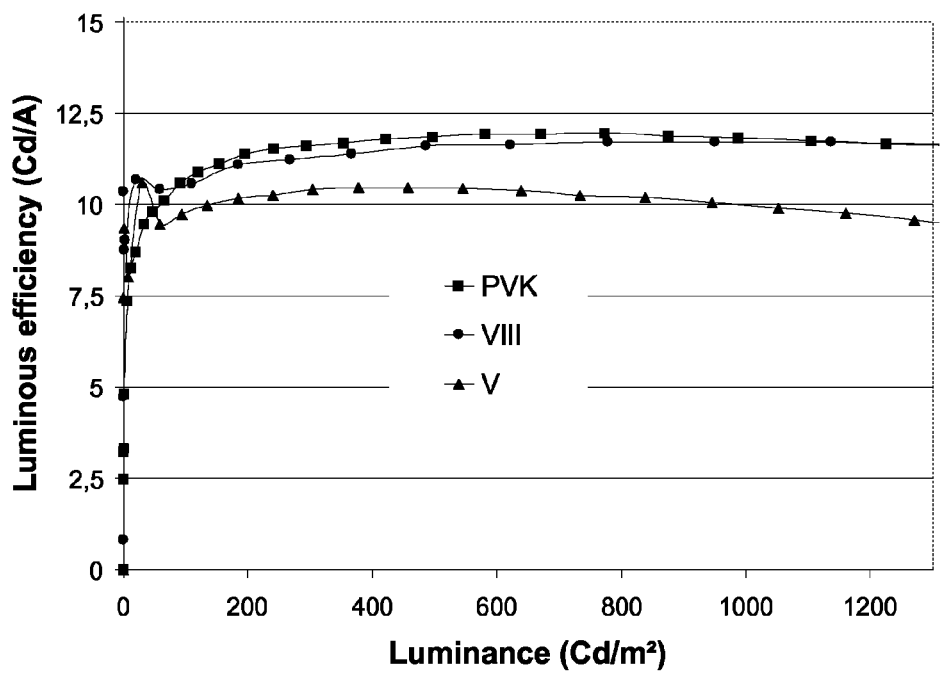
FIG. 10 shows the luminance efficiency curve of three OLED devices containing the compounds represented by formulae VIII and V versus reference material PVK (poly vinyl carbazole).

As shown in the FIG. 10 and in the table bellow, the devices involving the compounds VIII, V and the PVK have similar luminous efficiency in the range of 11 cd/A at 1000 cd/m² whereas V has lower efficiency around 9 cd/A at 1000 cd/m². The fact that voltage is lower for VIII compared to PVK results in an improvement of the power efficiency up to 4.8 lm/W. This clearly demonstrates the possibility to use the new hosts OLEDs containing solution processed EML with similar or even improved performance over PVK. The possibility to sublime those hosts materials which is not possible with PVK, could in principle enable improved lifetimes of OLED devices.

| at 1000 cd/m² | | | | | | |
| --- | --- | --- | --- | --- | --- | --- |
| Device | V | EQE | Lm/W | Cd/A | x | y |
| PVK | 11.0 | 4.7 | 3.3 | 11.4 | 0.19 | 0.42 |
| VIII | 8.5 | 5.4 | 4.8 | 11.7 | 0.16 | 0.38 |
| V | 9.7 | 4.3 | 3.1 | 9.5 | 0.17 | 0.38 |

It will be apparent to those skilled in the art that various modifications and variations can be made to the present invention without departing from the spirit and scope of the invention. Thus, it is intended that the present disclosure covers the modifications and variations of this invention, provided they come within the scope of the appended claims and their equivalents.

The invention claimed is:

1. A compound of Formula I:

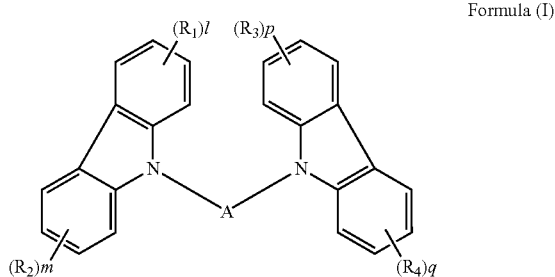

Formula (I)

wherein:

A is a divalent radical selected from the group consisting of naphthyl, anthryl, phenanthryl, benzamidazolyl, carbazolyl, fluorenyl, pyridazinyl, quinolinyl, isoquinolinyl, quinoxalinyl, benzothiophenyl, phthalazinyl, quinazolinyl, benzimidazolyl, benzoxazolyl, phenanthridinyl,

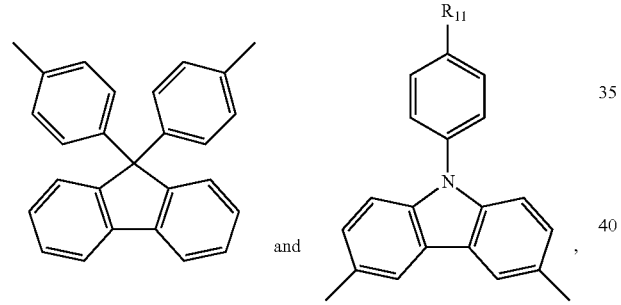

and wherein $R_{11}$ is a tert-alkyl, fluorinated alkyl, trityl, alkoxy or halogen group;

$R_1$, $R_2$, $R_3$ and $R_4$ are non-conjugate substituents, the same or different at each occurrence and selected from the group consisting of:
trityl
halogen;
nitro;
cyano;
—COOR$_5$;
alkoxy or dialkylamino group having from 1 to 20 carbon atoms wherein one or more nonadjacent —CH$_2$— groups may be replaced by —O—, —S—, —NR$_6$—, —CONR$_7$— or —COO— and wherein at least one hydrogen atom may be replaced by halogen; and
—SiR$_8$R$_9$R$_{10}$;

wherein $R_5$, $R_6$, $R_7$, $R_8$, $R_9$, and $R_{10}$ are the same or different at each occurrence and independently selected from the group consisting of —H, halogen, nitro, cyano, straight or branched $C_{1-20}$-alkyl, $C_{3-20}$-cyclic alkyl, straight or branched $C_{1-20}$-alkoxy, $C_{1-20}$-dialkylamino, $C_{4-14}$-aryl, $C_{4-14}$-aryloxy and $C_{4-14}$-heteroaryl, which may be substituted by one or more non aromatic radicals, wherein a plurality of $R_1$, $R_2$, $R_3$, $R_4$, $R_8$, $R_9$, and $R_{10}$ may in turn together form a mono- or polycyclic ring, optionally aromatic; and l, m, p and q are the same or different at each occurrence and represent an integer from 0 to 4, wherein l+m+p+q>0.

2. The compound of claim 1 wherein A is a divalent radical of Formula II:

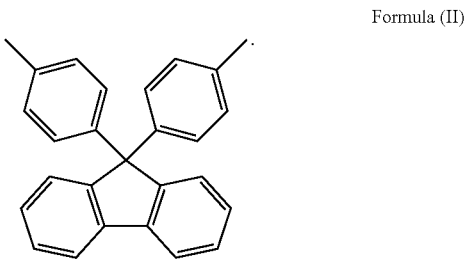

Formula (II)

3. The compound of claim 1 wherein A is a divalent radical of Formula III:

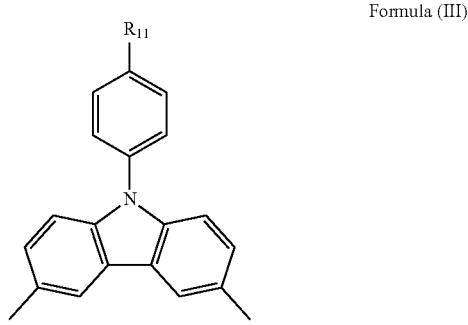

Formula (III)

wherein $R_{11}$ is an tert-alkyl, fluorinated alkyl, trityl, alkoxy or halogen group.

4. The compound of claim 1, wherein each of $R_1$, $R_2$, $R_3$ and $R_4$ is —SiR$_8$R$_9$R$_{10}$ and $R_8$, $R_9$, and $R_{10}$ are the same or different at each occurrence and independently selected from the group consisting of an alkyl group and an aryl group.

5. An organic light emitting device (OLED) comprising an emissive layer (EML), where the emissive layer comprises a host material which is the compound of claim 1.

6. The compound of claim 2, wherein each of $R_1$, $R_2$, $R_3$ and $R_4$ is —SiR$_8$R$_9$R$_{10}$ and $R_8$, $R_9$, and $R_{10}$ are the same or different at each occurrence and independently selected from the group consisting of an alkyl group and an aryl group.

7. The compound of claim 3, wherein each of $R_1$, $R_2$, $R_3$ and $R_4$ is —SiR$_8$R$_9$R$_{10}$ and $R_8$, $R_9$, and $R_{10}$ are the same or different at each occurrence and independently selected from the group consisting of an alkyl group and an aryl group.

8. The compound of claim 4, wherein each of $R_8$, $R_9$, and $R_{10}$ is an isopropyl group and each of l, m, p and q is 1.

9. The compound of claim 4, wherein the compound has the following formula:

Formula (VII)

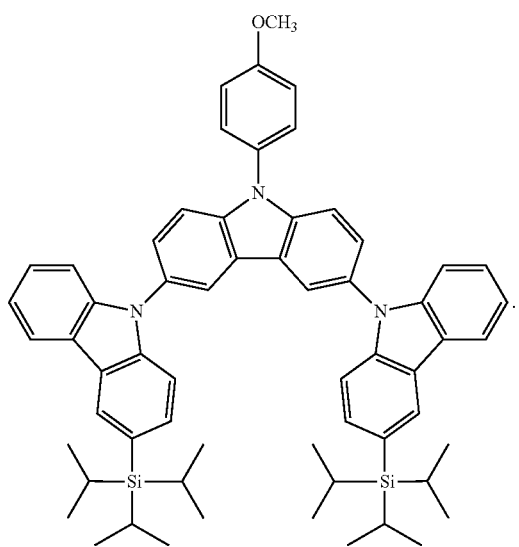

10. The compound of claim 4, wherein the compound has the following formula:

Formula (X)

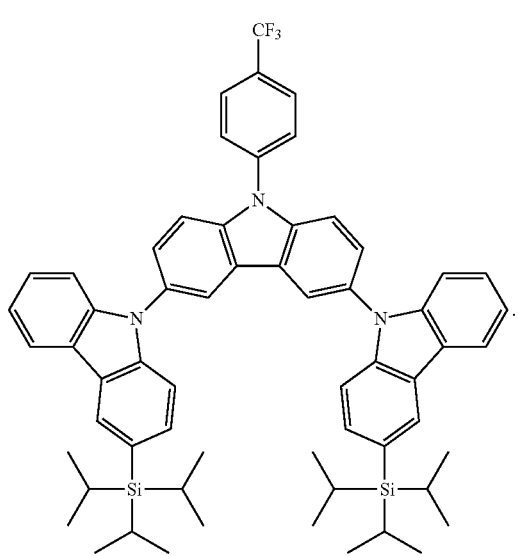

11. The compound of claim 4, wherein the compound has the following formula:

Formula (VIII)

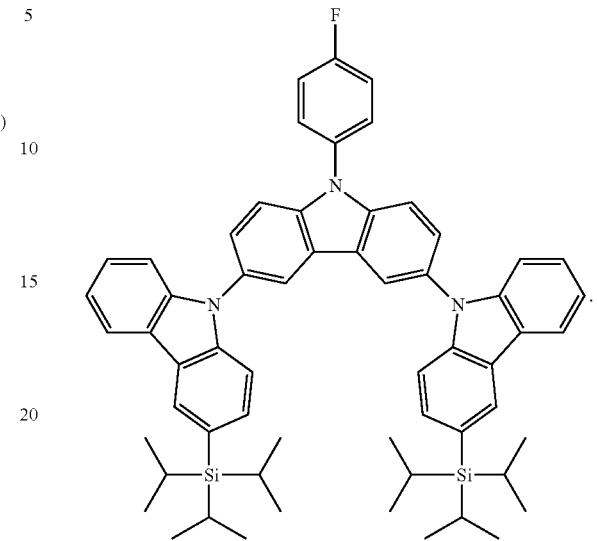

12. The compound of claim 4, wherein the compound has the following formula:

Formula (IX)

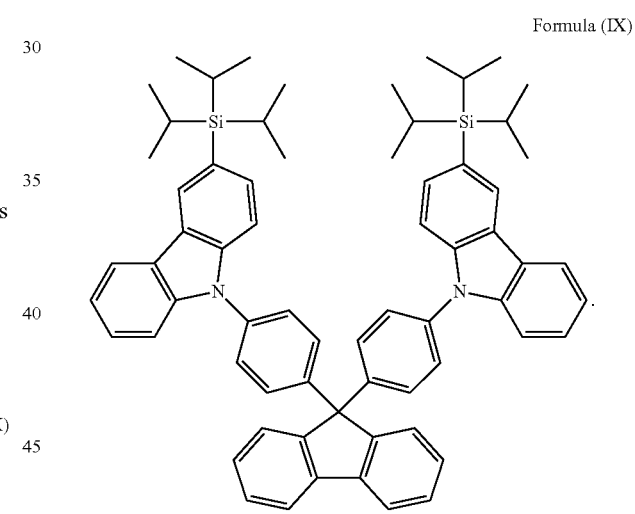

13. The organic light emitting device (OLED) of claim 5, wherein the host material is a compound having a formula selected from the group consisting of:

Formula (IV)

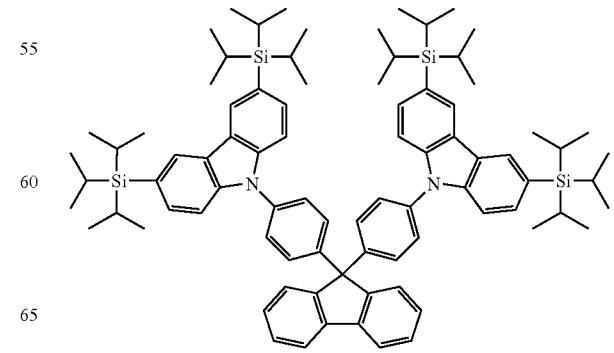

Formula (V)
Formula (VI)
Formula (VII)
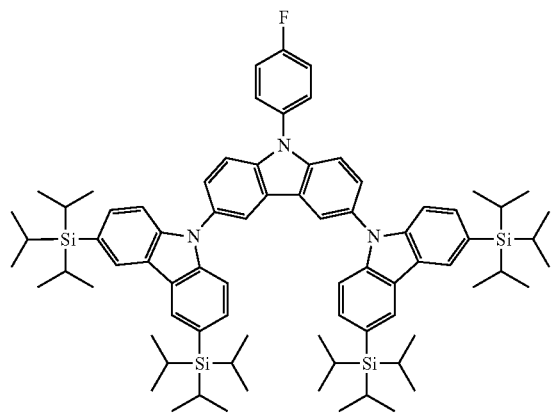
Formula (VIII)
Formula (IX)
Formula (X)
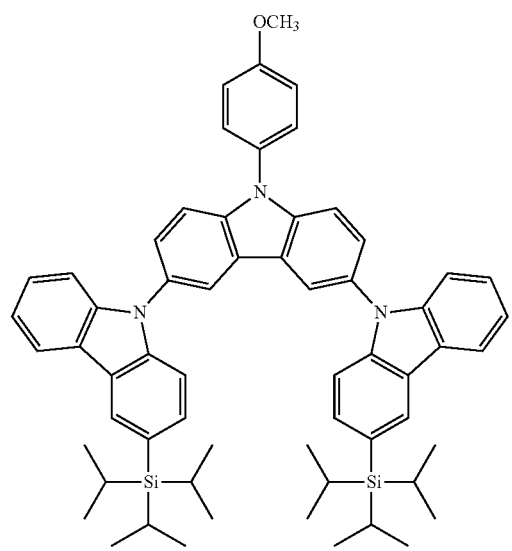
and -continued

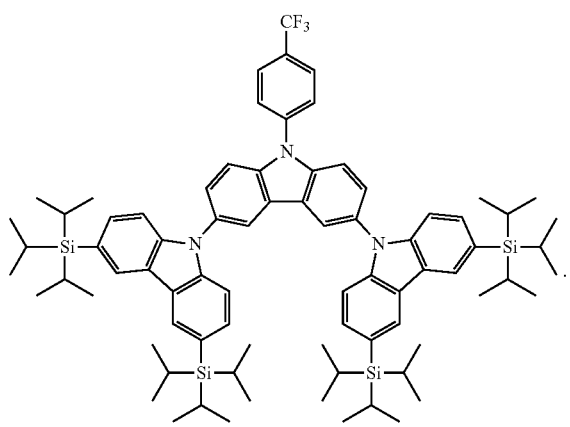

Formula (XI)

14. The organic light emitting device (OLED) of claim 5, which comprises:
- a glass substrate;
- a generally transparent anode;
- a hole transporting layer (HTL);
- the emissive layer (EML);
- an electron transporting layer (ETL); and
- a generally metallic cathode.

15. A method for emitting blue light, which comprises using the organic light emitting device (OLED) of claim 5.

16. The compound of claim 8, wherein the compound has the following formula:

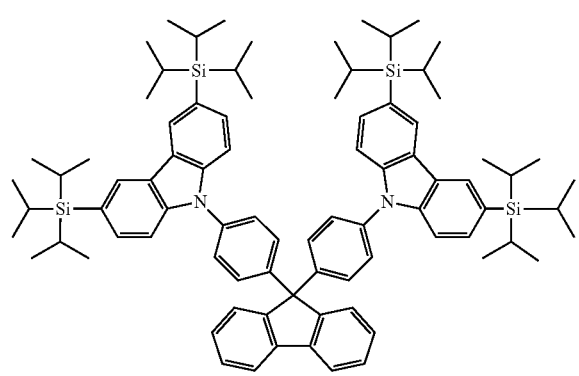

Formula (IV)

17. The compound of claim 8, wherein the compound has the following formula:

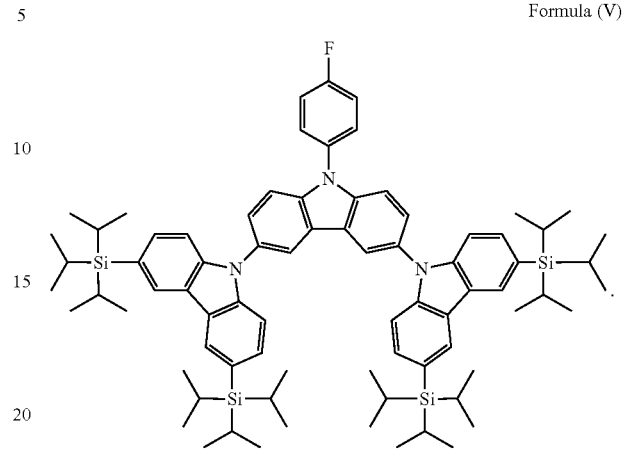

Formula (V)

18. The compound of claim 8, wherein the compound has the following formula:

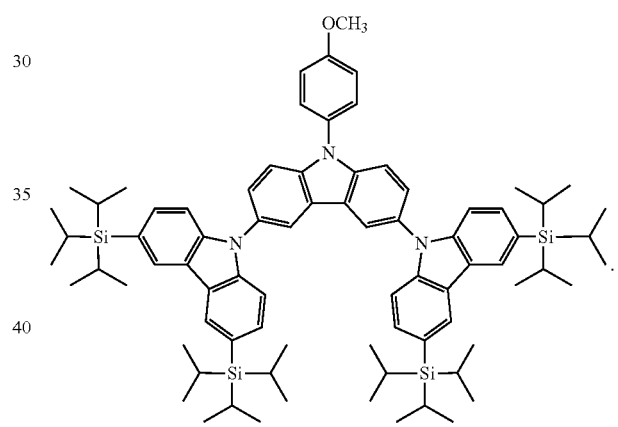

Formula (VI)

19. The compound of claim 8, wherein the compound has the following formula:

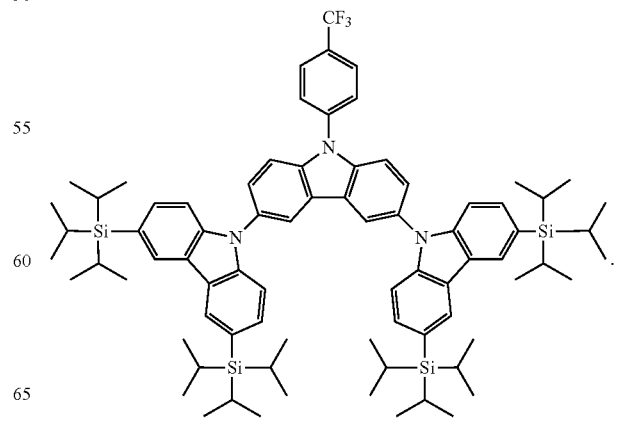

Formula (XI)

20. A method for emitting blue light, which comprises using the organic light emitting device (OLED) of claim 14.

* * * * *